(12) United States Patent
Tsenkova

(10) Patent No.: US 7,570,357 B2
(45) Date of Patent: Aug. 4, 2009

(54) VISIBLE/NEAR-INFRARED SPECTROMETRY AND ITS DEVICE

(75) Inventor: Roumiana Tsenkova, Kobe (JP)

(73) Assignee: Kyokko Denki Kabushiki Kaisha, Kobe (JP)

( * ) Notice: Subject to any disclaimer, the term of this patent is extended or adjusted under 35 U.S.C. 154(b) by 384 days.

(21) Appl. No.: 10/578,272

(22) PCT Filed: Nov. 10, 2004

(86) PCT No.: PCT/JP2004/016680

§ 371 (c)(1),
(2), (4) Date: Jan. 12, 2007

(87) PCT Pub. No.: WO2005/050176

PCT Pub. Date: Jun. 2, 2005

(65) Prior Publication Data

US 2007/0211247 A1 Sep. 13, 2007

(30) Foreign Application Priority Data

Nov. 10, 2003 (JP) .............................. 2003-379517

(51) Int. Cl.
G01J 3/28 (2006.01)
G01J 3/40 (2006.01)
(52) U.S. Cl. ...................................... 356/326; 356/303
(58) Field of Classification Search .......... 356/300–334
See application file for complete search history.

(56) References Cited

U.S. PATENT DOCUMENTS 4,785,806 A * 11/1988 Deckelbaum ................. 606/7
5,070,874 A * 12/1991 Barnes et al. ............... 600/316
5,813,403 A * 9/1998 Soller et al. ................. 600/310
6,485,703 B1 * 11/2002 Cote et al. ................... 424/9.1
6,765,668 B2 * 7/2004 Gardner et al. .............. 356/301

FOREIGN PATENT DOCUMENTS

| JP | 10-190 | 1/1998 |
| JP | 2002-5827 | 1/2002 |
| JP | 2002-156452 | 5/2002 |
| JP | 2002-543402 | 12/2002 |
| JP | 2003-42948 | 2/2003 |

* cited by examiner

Primary Examiner—L. G Lauchman
Assistant Examiner—Jarreas C Underwood
(74) Attorney, Agent, or Firm—Wenderoth, Lind & Ponack, L.L.P.

(57) ABSTRACT

A visible/near-infrared spectrometry and its device for determining the components of a sample and the characteristics of the components of the sample by using visible light and/or near-infrared light in the wavelength range from 400 nm to 2500 nm. This spectrometry and device enable measurement that has been conventionally difficult, including high-accuracy determination of many components, detection of components present in ultra-low concentrations, and real-time determination of component characteristics, including determination of the structure or function of bio-macromolecules and their variations. The spectrum of a sample is measured while exposing the sample to water-activating perturbations (WAP), thereby causing the response spectrum to change, and by detecting transitions of the response spectrum. With this, by conducting spectrum analysis and/or multivariate analysis, the components of the sample and/or the characteristics of the components can be determined.

19 Claims, 31 Drawing Sheets

Fig. 3
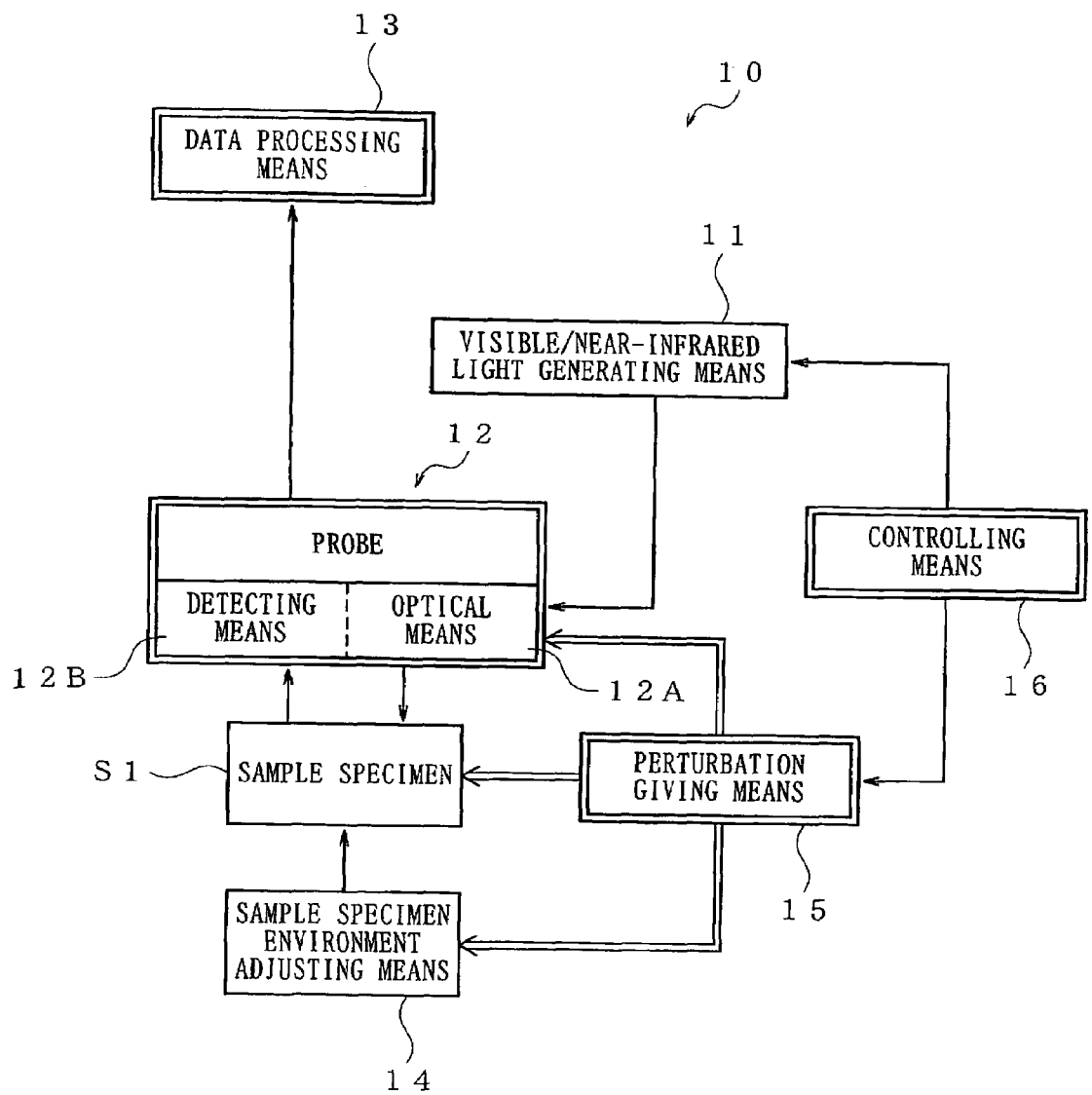
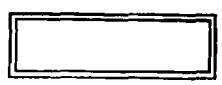 : CHARACTERISTIC PORTION OF THE PRESENT INVENTION DEVICE

Autopeaks: 606 nm, 628 nm, 640 nm, 678 nm, 738 nm, 750 nm, and 776 nm

2D-COS synchronous map, crosspeaks

Fig. 6

Autopeaks: 606 nm, 628 nm, 640 nm, 678 nm, 738 nm, 750 nm, and 776 nm

Synchronous

| λ [nm] x axis | λ [nm] y axis | | | | | | |
|---|---|---|---|---|---|---|---|
| 606 | 640 | 738 | 808 | | | | |
| 610 | 738 | | | | | | |
| 618 | 694 | | | | | | |
| 628 | 770 | | | | | | |
| 640 | 606 | 678 | 738 | 752 | 776 | 792 | 808 |
| 678 | 624 | 632 | 638-644 | | | | |
| 688 | 672 | | | | | | |
| 694 | 614 | 618 | 730 | 810 | | | |
| 696 | 730 | 810 | | | | | |
| 704 | 764 | | | | | | |
| 710 | 624 | 632 | 642 | 808 | | | |
| 738 | 606 | 610 | 640 | 752 | 776 | 792 | 808 |
| 752 | 640 | 738 | | | | | |
| 770 | 628 | | | | | | |
| 772 | 764 | | | | | | |
| 776 | 610 | 640 | 738 | 792 | 810 | | |
| 792 | 606 | 610 | 640 | 738 | 776 | 808 | |
| 808 | 606 | 640 | 694 | 738 | 776 | 792 | |
| 810 | 640 | 678 | 680 | 682 | 694 | 738 | 776 |

2D-COS synchronous map, crosspeaks

CNS bacteria Regression Vector. Important wavelengths: 1406-1500nm, 1180nm-1306nm CPS Regression vector.
Important wavelengths: 740nm, 770nm, 808nm, 1156-1198nm, 1466nm, 1476nm, 1650nm, 1686nm, 1704nm, 1720nm, 1750nm, 1846nm, 1890nm

Fig. 12

| CPS | | | | | | | | |
|---|---|---|---|---|---|---|---|---|
| | Percent | cumulative | SEV | Press Val | r Val | SEC | Press Cal | r Cal |
| Factor6 | 0.952331 | 97.56091 | 3.096218 | 316.3566 | 0.944926 | 0.674208 | 11.81845 | 0.996617 |

| CNS | | | | | | | | |
|---|---|---|---|---|---|---|---|---|
| | Percent | cumulative | SEV | Press Val | r Val | SEC | Press Cal | r Cal |
| Factor 9 | 0.000002 | 99.99999 | 3.04932 | 306.8456 | 0.909211 | 0.638169 | 9.774219 | 0.997202 |

THREE-DIMENSION SCORE PLOT
PCA PRINCIPAL COMPONENT

RESULT OF SIMCA ANALYSIS

INTERCLASS DISTANCE BETWEEN CNS AND CPS

| | SAMPLE・WAVELENGTH SELECTION | DISTANCE |
|---|---|---|
| A1 | WATER EXCLUDE (Autoscale,Smooth(15),2nd Derivative(25)) | 0.836 |
| A2 | WATER, NOISE EXCLUDE (Autoscale,Smooth(15),1st Derivative(25)) | 0.823 |
| A3 | WATER, NOISE EXCLUDE (Autoscale,Smooth(15),2nd Derivative(25)) | 0.984 |
| A4 | WATER, BPW, NOISE EXCLUDE (Autoscale,Smooth(15),1nd Derivative(25)) | 1.156 |
| A5 | WATER, BPW, NOISE EXCLUDE (Autoscale,Smooth(15),2st Derivative(25)) | 1.826 |
| A6 | WATER, BPW, DILUTED SAMPLE, NOISE EXCLUDE, 3TIMES (Autoscale,Smooth(15),1st Derivative(25)) | 4.254 |
| A7 | WATER, BPW, DILUTED SAMPLE, NOISE EXCLUDE (Autoscale,Smooth(15),2nd Derivative(25)) | 2.103 |
| A8 | WATER, BPW, DILUTED SAMPLE, NOISE EXCLUDE, 1TIME (Autoscale,Smooth(15),1st Derivative(25)) | 4.132 |

(b)

| | Pred. CNS | Pred.CPS | No match |
|---|---|---|---|
| CNS | 34.0000 | 0.0000 | 0.0000 |
| CPS | 0.0000 | 36.0000 | 0.0000 |

Fig. 16

Table 2  SIMCA Interclass Distance

|        | PrP-Cu | PrP-Mn | PrP  |
|--------|--------|--------|------|
| PrP-Cu | 0.00   | 28.81  | 4.15 |
| PrP-Mn | 28.81  | 0.00   | 11.44 |
| PrP    | 4.16   | 11.44  | 0.00 |

Fig. 18

SIMCA distances between PrP isomers increases when dissolved in water

|     | 1.0 mg/ml concentrartion | | |
| --- | --- | --- | --- |
|     | CS2@2 | CS3@1 | CS4@2 |
| CS2 | 0.000000 | 0.861595 | 0.652900 |
| CS3 | 0.861595 | 0.000000 | 1.781953 |
| CS4 | 0.652900 | 1.781953 | 0.000000 |

|     | 0.5 mg/ml concentrartion | | |
| --- | --- | --- | --- |
|     | CS2@1 | CS3@1 | CS4@1 |
| CS2 | 0.000000 | 2.434433 | 0.543989 |
| CS3 | 2.434433 | 0.000000 | 2.806436 |
| CS4 | 0.543989 | 2.806436 | 0.000000 |

|     | 0.1 mg/ml concentrartion | | |
| --- | --- | --- | --- |
|     | CS2@2 | CS3@2 | CS4@1 |
| CS2 | 0.000000 | 2.674993 | 1.163065 |
| CS3 | 2.674994 | 0.000000 | 1.788170 |
| CS4 | 1.163065 | 1.788170 | 0.000000 |

|     | 0.05 mg/ml concentrartion | | |
| --- | --- | --- | --- |
|     | CS2@1 | CS3@1 | CS4@1 |
| CS2 | 0.000000 | 7.862999 | 8.612659 |
| CS3 | 7.862999 | 0.000000 | 5.843394 |
| CS4 | 8.612659 | 5.843394 | 0.000000 |

CS2: PrP(Cu) in Water

CS3: PrP in Water

CS4: PrP in W(Cu) (water with cupper)

(a)

(b)

Interclass Distance: SIMCA

|  | Class1 | Class2 | Class3 |
|---|---|---|---|
| Class PrP(Cu) Class:1 | 0.0 | 1.19 | 24.84 |
| Class PrP Class:2 | 1.19 | 0.0 | 26.43 |
| Class PrP in W(Cu) Class:3 | 24.84 | 26.43 | 0.0 |

(c)

Misclassification SIMCA

|  | Pred1 | Pred2 | Pred3 | No match |
|---|---|---|---|---|
| Actual Class 1 | 13.00 | 0.00 | 0.00 | 0.00 |
| Actual Class 2 | 0.00 | 13.00 | 0.00 | 0.00 |
| Actual Class 3 | 0.00 | 0.00 | 13.00 | 0.00 |

Fig. 21

SIMCA distances between PrP isomers increases when dissolved in water
Each PrP sample is analysed at
4 different temperatures: 21°C, 30

(a)

(b)

| Factor9 (3回) | Percent 0.009203 | cumulative 99.94567 | SEV 1.008785 | Press Val 14.24707 | r Val 0.866991 | SEC 0.026814 | Press Cal 0.002876 | r Cal 0.999969 |
|---|---|---|---|---|---|---|---|---|
| Factor5 (1回) | Percent 1.745422 | cumulative 99.94188 | SEV 3.558607 | Press Val 88.64576 | r Val 0.85991 | SEC 0.41932 | Press Cal 0.17583 | r Cal 0.99679 |

(c)

| InterClassDistance (SIMCA, raw spectra, mean-center, smoothing 25nm) | PCA Factors |
|---|---|
| 1 | 8.65 | 4 |
| 1 & 2 | 9.79 | 4 |
| 1 & 2 & 3 | 10.11 | 4 |

(a)

(b)

| Factor6 (3回) | Percent | cumulative | SEV | Press Val | r Val | SEC | Press Cal | r Cal |
|---|---|---|---|---|---|---|---|---|
| | 0.116864 | 99.8904 | 0.466675 | 8.058082 | 0.951239 | 0.379212 | 4.314054 | 0.973881 |
| Factor5 (1回) | Percent | cumulative | SEV | Press Val | r Val | SEC | Press Cal | r Cal |
| | 6.582126 | 98.31849 | 0.937039 | 3.512166 | 0.893979 | 0.357026 | 0.127468 | 0.992689 |

SIMCA DISTANCE of Granul/Powder Coffee serially diluted with water

| CONCENTRATION AFTER DILUTION | SIMCA DISTANCE |
|---|---|
| 1% | 15.96 |
| 2% | 5.98 |
| 3% | 7.16 |
| 4% | 6.77 |

(b)

SIMCA DISTANCE of Granul/Powder Sugar serially diluted with water

| CONCENTRATION AFTER DILUTION | SIMCA DISTANCE |
|---|---|
| 0.50% | 5.15 |
| 1% | 4.51 |
| 2% | 7.6 |
| 4% | 1.59 |

(c)

SUGAR Concentartion measurement, PLS regression (0.5,1,2,4%)

|  | Rv (Serial Dilution) | SEV (Serial Dilution) |
|---|---|---|
| Granul | 0.995 | 0.0438 |
| Powder | 0.9998 | 0.0258 |

Fig. 26

Blood Plasma Spectra – Milk Component Estimation (a) Table 3-1. Relationship between first 10 principal components of blood plasma spectra and milk components

| Parameter | min | max | average | The best way of data transf. | R |
|---|---|---|---|---|---|
| Fat, % | 2.00 | 5.47 | 3.41 | Log(1/T) | 0.698 |
| Crude Protein, % | 2.88 | 4.05 | 3.32 | D1 | 0.685 |
| Casein, % | 2.18 | 2.87 | 2.62 | D1 | 0.728* |
| True protein, % | 2.74 | 3.87 | 3.17 | D1 | 0.683 |
| MUN, % | 1.40 | 3.10 | 2.00 | Log(1/T) | 0.546 |
| Lactose, % | 4.12 | 4.93 | 4.54 | Log(1/T) | 0.534 |

Statistically significant at: * P<0.05

(b) Table 3-2. NIRS calibration and validation results for estimation of milk composition from the spectra of blood plasma by PLS regression

| Parameter | The best way of data transf. | PLS factors | SEC | R | SECV |
|---|---|---|---|---|---|
| Fat, % | Log(1/T) | 2 | 0.612 | 0.575 | 0.692 |
| Crude protein, % | D1 | 4 | 0.208 | 0.829*** | 0.377 |
| Casein, % | D1 | 6 | 0.108 | 0.938*** | 0.273 |
| True protein, % | D1 | 4 | 0.133 | 0.863*** | 0.281 |
| MUN, % | Log(1/T) | 5 | 0.248 | 0.938*** | 0.584 |
| Lactose, % | D1 | 3 | 0.177 | 0.596 | 0.239 |

Statistically significant at: *** P<0.001

Milk Spectra – Blood Plasma Component Estimation (c) Table 3-3. Relationship between first 10 principal components of milk spectra and some components of blood plasma

| Parameter | min | max | average | The best way of Data transf. | R |
|---|---|---|---|---|---|
| Albumin, % | 2.87 | 3.58 | 3.25 | Log(1/T) | 0.624 |
| Glucose, mg/dl | 45.9 | 72.7 | 61.6 | Log(1/T) | 0.361 |
| BUN, % | 11.3 | 21.2 | 15.9 | Log(1/T) | 0.618 |

(d) Table 3-4. NIRS calibration and validation results for estimation of blood plasma composition from the spectra of milk by PLS regression

| Parameter | The best way of data transf. | PLS factors | SEC | R | SECV |
|---|---|---|---|---|---|
| Albumin, % | Log(1/T) | 7 | 0.174 | 0.718** | 0.202 |
| Glucose, mg/dl | Log(1/T) | 4 | 4.588 | 0.322 | 4.691 |
| BUN, % | D1 | 8 | 1.771 | 0.682* | 1.969 |

Statistically significant at: * P<0.05 ** P<0.01

Fig. 27

Rumen Juice Spectra – Milk Component Estimation (a) Table 4-1. Relationship between first 10 principal components of rumen juice spectra and milk components

| Parameter | min | max | average | The best way of Data transf. | R |
|---|---|---|---|---|---|
| Fat, % | 2.00 | 5.47 | 3.41 | D1 | 0.750* |
| Crude Protein, % | 2.88 | 4.05 | 3.32 | D2 | 0.703 |
| Casein, % | 2.18 | 2.87 | 2.62 | D2 | 0.826** |
| True protein, % | 2.74 | 3.87 | 3.17 | D2 | 0.698 |
| MUN, % | 1.40 | 3.10 | 2.00 | Log(1/T) | 0.665 |
| Lactose, % | 4.12 | 4.93 | 4.54 | D1 | 0.593 |

Statistically significant at: * P<0.05 ** P<0.01

(b) Table 4-2. NIRS calibration and validation results for estimation of milk composition from the spectra of rumen juice by PLS regression

| Parameter | The best way of data transf. | PLS factors | SEC | R | SECV |
|---|---|---|---|---|---|
| Fat, % | Log(1/T) | 5 | 0.455 | 0.766*** | 0.583 |
| Crude protein, % | D2 | 4 | 0.138 | 0.890*** | 0.231 |
| Casein, % | D2 | 5 | 0.091 | 0.902*** | 0.191 |
| True protein, % | D2 | 4 | 0.139 | 0.826*** | 0.241 |
| MUN, % | Log(1/T) | 7 | 0.161 | 0.942*** | 0.393 |
| Lactose, % | Log(1/T) | 3 | 0.204 | 0.283 | 0.232 |

Statistically significant at: *** P<0.001

Milk Spectra – Rumen Juice Component Estimation (c) Table 4-3. Relationship between first 10 principal components of milk spectra and some components of rumen juice

| Parameter | min | max | average | The best way of Data transf. | R |
|---|---|---|---|---|---|
| PH | 5.4 | 6.5 | 6.27 | Log(1/T) | 0.515 |
| $NH_3$-N | 2.2 | 18.8 | 8.42 | Log(1/T) | 0.516 |
| $C_2$ | 50.4 | 64.6 | 58.6 | Log(1/T) | 0.555 |
| $C_3$ | 16.9 | 36.1 | 23.1 | Log(1/T) | 0.532 |
| $C_4$ | 11.1 | 19.0 | 14.7 | Log(1/T) | 0.457 |

(d) Table 4-4. NIRS calibration and validation results for estimation of rumen juice composition from the spectra of milk by PLS regression

| Parameter | The best way of data transf. | PLS factors | SEC | R | SECV |
|---|---|---|---|---|---|
| PH | Log(1/T) | 4 | 0.26 | 0.471 | 0.27 |
| $NH_3$-N | Log(1/T) | 7 | 3.70 | 0.649* | 4.22 |
| $C_2$ | Log(1/T) | 7 | 3.02 | 0.692** | 3.56 |
| $C_3$ | Log(1/D) | 7 | 3.48 | 0.686* | 4.06 |
| $C_4$ | Log(1/T) | 6 | 1.71 | 0.569 | 1.89 |

Statistically significant at: * P<0.05 ** P<0.01

Fig. 28
(a)
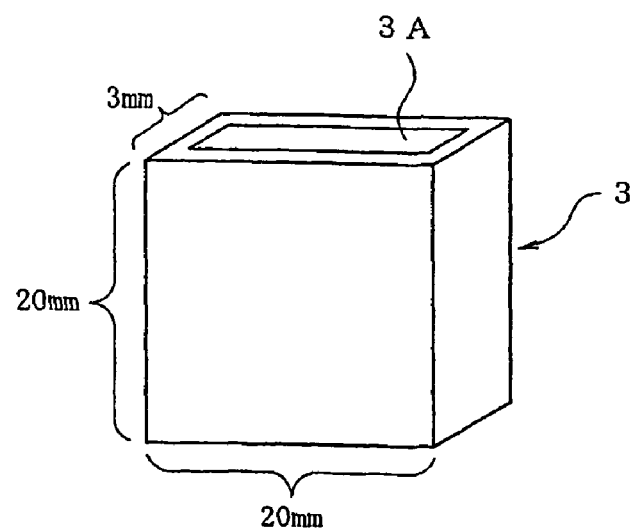
(b)
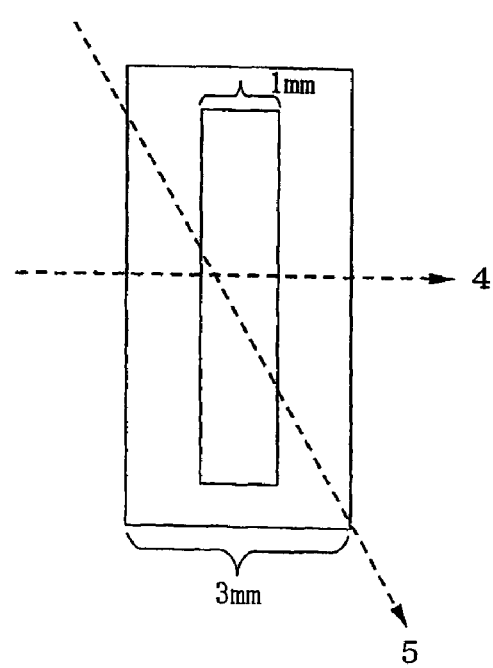

(a)

Important Wavelengths: 534nm, 620nm, 688nm, 694nm, 778nm, 844nm, 858nm, 940nm (b)

|  | Factors | SEV | r Val | SEC | r Cal |
|---|---|---|---|---|---|
| Without EMF | Factor10 | 0.204269 | 0.980037 | 0.136665 | 0.994630 |
| After Applying EMF | Factor9 | 0.087212 | 0.996256 | 0.067217 | 0.998611 |
| In the presence of EMF | Factor9 | 0.071528 | 0.997483 | 0.056339 | 0.999024 |

VISIBLE/NEAR-INFRARED SPECTROMETRY AND ITS DEVICE

TECHNICAL FIELD

The present invention relates to visible/near-infrared spectrometry and its device for determining the components and characteristics of a sample specimen through spectral analysis and/or multivariate analysis of the absorption spectrum.

BACKGROUND

Recently, component analysis using visible and/or near-infrared light irradiated on a given sample to determine the wavelength or wavelength range absorbed by specific components in that sample has been conducted in various fields to determine the characteristics of those specific components.

Such a process is achieved by injecting a sample into a quartz cell, then irradiating the cell with visible and/or near-infrared light in the wavelength range of 400 nm to 2500 nm and using the near-infrared spectrograph (e.g. NIRSystem 6500 manufactured by Nireco Co.), and then analyzing the transmitted light and the reflected light, or transmitted/reflected light (henceforth referred to as transmitted/reflected light).

Generally, near-infrared light is a low-energy magnetic wave which means that the use of such a low-energy magnetic wave does not alter nor damage the basic characteristics of the materials or sample under scrutiny.

Therefore, relevant information can directly and immediately be obtained by detecting the spectral intensity of transmitted and reflected light and conducting multivariate analysis by using absorption rate data.

Already disclosed, is the method of getting sample information by consecutively obtaining multiple spectra from light irradiation in the wavelength range of 400 nm to 2500 nm and/or a wavelength suitable to obtain the needed data for a specific sample. After the sample is irradiated, multivariate analysis of the water molecule peaks allows identification of the elements and provides the basis for the construction of model. (Patent document 1)

Furthermore, multivariate analysis of the absorbance rate data of visible and/or near infrared light in water molecules provides a method for measuring the presence of somatic cells in raw milk and, as a result, becomes an additional means of diagnosing mastitis in cows (Ref. e.g. Patent Document 2).

Patent document 1: Japanese Published Unexamined Application 2002-5827 (Pages 1 to 9, FIG. 1)

Patent document 2: International Publication WO01/75420 (Pages 1 to 5, FIG. 1)

DISCLOSURE OF INVENTION

Problems to be Solved

The conventional method uses visible and/or infrared spectrometry to obtain component information on the subject sample. That information is obtained by irradiating light in a wavelength range of 400 nm to 2500 nm, under various conditions and then detecting element peak changes of water molecules spectra due to the interaction between the water molecules present in the sample and target components in the subject specimen. Such a method has limitations as to what components are measurable and also as to measurement accuracy.

The purpose of the present invention claims to present a visible/near-infrared spectrometry method and its devices to enable component identification at ultra-low concentrations using light in the wavelength range from 400 nm to 2500 nm and in real time. That feat has traditionally been difficult to achieve. The new method provides high-accuracy identification of a component and its characteristics, as well and provides precise information on the structure and/or functions of bio-molecules and their variations.

Means to Solve the Problems

A method of the present invention related to claim 1 in order to realize the above object is a visible/near infrared spectrometry comprising following steps of:

irradiating a sample specimen with visible light and/or near-infrared light in the wavelength range from 400 nm to 2500 nm or in part of that range;

analyzing the spectra of transmitted light, reflected light, and/or transmitted/reflected light obtained from the sample specimen;

determining the presence and/or measuring the characteristics of respective specific components present in said sample specimen, wherein said method further comprises steps of;

measuring spectra while giving predetermined conditions including at least 3 times repeated irradiations as conditions to generate transitional changes of spectral response pattern while activating water existing within and/or around said sample specimen to promote interaction between water molecules and predetermined component included in said sample specimen;

conducting spectral and/or multivariate analysis to detect transitional changes in spectral response patterns;

building a model assuming that components of known sample specimen can be determined and/or a model assuming that characteristics of said components can be measured using the detected transitional changes of the spectral response patterns;

conducting the same spectral and/or multivariate analysis on unknown(new) sample specimen while giving the same conditions as said predetermined conditions: and, comparing with the built models to predict components of unknown sample specimen and/or characteristics of the components.

According to the previous claim 1, the invention makes it possible to establish a model of the correlations of transitional changes arising from adding predetermined conditions while acquiring spectra, and the spectral response to those changes, a feat that has conventionally been difficult to measure. Furthermore, the method makes it possible to measure the concentration of specific components as well as granule diameter. And causes extremely small alterations in the sample specimen and thus makes it possible to detect and measure very small changes caused by specific components when giving specific predetermined conditions and conducting spectral and/or multivariate analysis. The transitional changes of the spectral response patterns of water molecules on the spectral graph are so small that they cannot be detected by the human eye but the invention presented here enables high-accuracy determination of component characteristics and further detection of ultra-low concentrations of those components in real time.

In the invention related to claim 3, said predetermined condition changes are perturbations (water activating perturbations: WAP) to induce physical or chemical changes to said sample specimen by activating water existing within and/or around said sample specimen, and the perturbations are any one or a combination of at least 3 times repeated light irradiations, change of sample specimen concentration, extension of irradiation time, electromagnetic force application, light path-length changes, temperature changes, pH changes, and pressure changes.

According to the previous claim 3, this invention makes it also possible to select predetermined one or/and more Water Activated Perturbations (WAP) according to specific types of sample specimens.

In the invention related to claim 4, the concentrations of sample specimen are changed in step value by a factor of 10 (e.g. $10^{-1}$ to $10^{-10}$) to promote interaction between water and predetermined components, and respective concentrations are subjected to at least 3 times repeated irradiations to promote an interaction between water and the predetermined components.

According to the previous claim 4, the sample specimen concentrations are changed by dilution in a wide range which intensifies the interaction between the water molecules and pre-determined components present in the sample specimen so that changes in spectral patterns peaks can clearly be found and identified. Minimum concentrations of components can in this way clearly be both detected and measured.

In the invention related to claim 5, the invention allows the detection and identification of bacteria such as CNS (coagulase-negative *staphylococcus*) and CPS (coagulase-positive *staphylococcus*) when present in the sample specimen.

According to the previous claim 5, the invention makes it possible to construct models for high-accuracy identification of bacteria such as CNS (coagulase-negative staphylococcus) and CPS (coagulase-positive *staphylococcus*). That is achieved through the use of specific WAP perturbations as step changes by a factor of 10 in bacteria concentrations followed by multiple consecutive irradiations.

In the invention related to claim 6, spectrometry, with perturbation as changing concentration or dilution levels by a factor of 10 and subjecting those changes to at least 3 consecutive irradiations, allows detection of PrP(CU) and/or PrP (Mn) proteins with metal components and PrP proteins without metal components present in the sample specimen.

Furthermore and in relation to claim 6, changes in the spectral responses to perturbations in specific wavelengths are obtained by giving perturbations (WAP) in which repeated irradiations performed at specific time intervals. And through spectrometry of that spectral responses, a model can be constructed which makes it possible to find out if the specimen sample contains PrP(CU) and/or PrP(Mn) proteins with or without metal components.

In the invention related to claim 7, the spectrometry is conducted while giving perturbations in light path-length and/or concentrations are changed and respective changed samples are subjected to at least three times consecutive repeated irradiations. That procedure allows detection of PrP proteins with metal components and PrP proteins without metal components.

According to the previous claim 7, through conducting spectrometry of the sample specimen changing light path-length and/or concentrations while subjecting to consecutive irradiations of plural times for giving perturbations to allow detection of PrP(metal) proteins with metal components and PrP proteins without metal components.

In the invention related to claim 8, spectrometry is conducted while giving perturbations in which sample specimen concentrations are changed in step values by a factor of 10 and the respective changed samples are then subjected to consecutive irradiations, to measure antigen concentrations in the sample specimen.

According to the previous claim 8, the model can be built in such a way that the detection and measurement of antigens concentrations when present in the specimen sample by giving a perturbation(WAP) in which sample specimen concentrations are changed in step values (by a factor of 10) and a perturbation (WAP) in which respective changed samples are subjected to consecutive irradiations of plural times.

In the invention related to claim 9, the spectrometry is conducted while giving perturbations in which sample specimen concentrations are changed in step values and newly obtained samples are subjected to at least 3 times consecutive irradiations, to measure a diameter of pre-dissolved state of granule dissolved in the sample.

According to the previous claim 9, the model can be built in such that granule diameter in the pre-dissolved state can be measured by giving a perturbation (WAP) in which sample specimen concentrations are changed in step values and a perturbation (WAP) in which respective changes are subjected to consecutive irradiations of plural times.

In the invention related to claim 10, the detection of bacteria in the sample specimen is achieved through spectroscopy conducted while giving perturbations in which sample specimen concentrations are changed in step values by a factor of 10 and at least 3 consecutive irradiations.

According to the previous claim 10, the model can be built in such that even very low concentrations of different bacteria types can be detected by giving WAP perturbations as concentration changes (by a factor of 10) and subjecting the sample to consecutive irradiations of plural times.

In the invention related to claim 11, the application method of the invention states that spectrometry of the sample specimen should be conducted every morning and every evening for several consecutive days and again after changing the feed given to each animal as a perturbation, to estimate component concentrations of biological fluids including blood plasma and rumen juice of mammals such as cows based on raw milk spectra of the mammals.

According to the previous claim 11 the model can be built in such a way that biological information of mammals such as cows can be obtained easily by evaluating and/or measuring component concentrations of blood plasma and rumen juice through spectrometry of raw milk from mammals such as cows while giving WAP perturbations to the milk samples under investigation performed at different measurement intervals and measurement number of times (consecutive irradiations).

In the invention related to claim 12, spectrometry is to be conducted once every morning and once every evening for several consecutive days, after feeds to the sample specimen have been changed, to estimate the component concentrations of raw milk of the mammals such as cows based on the spectra of biological fluids including blood plasma and rumen juice of the mammals.

According to the previous claim 12, the model can be built in which quality characteristics of raw milk produced by dairy cows or other mammals can easily be estimated through spectrometry of biological fluids, including blood plasma and rumen juice, after WAR perturbations are performed and measurement intervals and measurement number of times are changed.

In the invention related to claim 13 the spectrometry is conducted while giving perturbations as changing the path-length while consecutively irradiation at least 3 times and using two sets of wave-lengths, that is, a first set ranging from 700 nm to 1100 nm and a second set ranging from 1100 nm to 2400 nm will allow measurements of multiple components present in raw milk.

According to the previous claim 13, the highly accurate measurements model of specific components can be achieved even within the range of short waves lengths, if spectrometry is performed changing light path-lengths.

In the invention related to claim 14, the spectrometry is conducted while giving perturbations in which 10 V. voltage is applied and light in the wavelength range 500 to 1000 nm is consecutively irradiated at least 3 times, to measure fat concentration in raw milk.

According to the previous claim 14, the model can be built in such that measuring fat concentration in raw milk by giving WAP perturbations, subjecting the sample to a changing electro-magnetic field and multiple consecutive irradiations.

A visible/near-infrared spectrometry device used in the present invention and related to claim 15 include:

a near-infrared light generating means capable of irradiating a sample specimen with near-infrared light or visible and/or near-infrared light in the wavelength range from 400 nm to 2500 nm or part of that range;

an optical means for irradiating said visible light and/or near-infrared light to the sample specimen;

a detecting means for obtaining spectra of transmitted light, reflected light, or transmitted/reflected light from said sample specimen; and a data processing means for conducting a predetermined multivariate analysis on obtained spectra, wherein the visible/near-infrared spectrometry device further comprises: a perturbation giving means for giving perturbations by adding predetermined condition changes to the sample to generate transitional changes in spectral response of activated water existing within and/or around said sample specimen to promote interaction between water molecules and specific component included in said sample specimen; and said data processing means conducting a spectral analysis on all or a part of the wavelength range of spectral responses obtained by giving perturbations.

According to the spectrometry device described at claim 15, that spectral responses to transitional changes can be detected and analyzed and that components can clearly be identified, which up to now had been difficult to achieve. And a characteristic of each component such as the concentration and the granule size can be measured.

In the invention related to claim 16, said perturbation giving means exposes the sample specimen to water activating perturbations (WAP) to induce physical or chemical changes to said sample specimen by activating water existing within and/or around said sample specimen, and comprises an irradiation controlling unit for controlling irradiation time and irradiation frequency is provided.

According to the previous claim 16, spectral response patterns in water molecules according to the addition of specific perturbations to the sample specimen can be accurately measured. In fact, very minute changes are detectable and analyzable. Therefore, ultra-low concentrations of specific components become detectable and the measurement of their characteristics becomes possible in real time.

In the invention related to claim 17, said perturbation giving means comprises at least one means capable of adjusting electromagnetic power, changing light path-length, and changing temperature; and a controlling means for controlling perturbations given by said perturbation giving means and operation timing between irradiating light and receiving light so as to irradiate light and receive light from probes which comprises said optical means and said detecting means together or separately and perform data processing.

According to the previous claim 17, provides the means for elaborating a model that will allow detection of ultra-low concentrations of any component, a feat that hitherto had been elusive or at least difficult to achieve.

In the invention related to claim 18, the execution of the spectral analysis of the responses to specific perturbations followed by data analysis for all or part of several distinct wavelengths ranges will allow the detection of bio-molecular structures and their functions and these changes.

Furthermore, and in relation to claim 18 the detection of bio-molecular structures and their respective functions and these changes can be obtained, in real time, by analyzing spectral changes caused by predetermined WAP perturbations and their effect on spectral response.

The device of the invention related to claim 19 comprises:

a sample specimen containing unit;

a perturbation giving means for giving perturbations by adding predetermined conditions to the sample specimen;

an optical means for irradiating visible light and/or near-infrared light in the wavelength range 400 nm to 2500 nm or part of the range to the sample specimen, said lights being in a predetermined specific wavelength range corresponding to sample specimen;

a detecting means for obtaining spectra of transmitted light, reflected light, or transmitted/reflected light from said sample specimen;

a data processing means for conducting a predetermined multivariate analysis on obtained spectra; and a displaying means for display a measurement result.

According to the spectrometry device described at claim 19, specific components in a sample specimen can be measured through the analysis of spectral responses to those components in the near-infrared wavelength range, while giving WAP perturbations.

The device of the invention related to claim 20 implements a spectroscopic method through the use of visible/near-infrared spectrometry (claimed in any one of claim 6 to claim 15) through the use of discrete and optimal important wavelengths appropriate for the analysis of specific sample specimens.

In relation to claim 20 the spectrometry is conducted in important wavelengths range that is optimal for a specific sample specimen to enable easy measurement of specific components.

Advantages of the Invention

Visible/near-infrared spectrometry and its device are used in the present invention, together with purposeful perturbations (water activating perturbations: WAP) in order to activate water existing within and/or around the sample specimen. This is achieved by adding predetermined conditions to a sample specimen and observing the spectral response patterns to those perturbations, including predetermined water spectra which change depending on the respective components present in the sample specimen. Those changing patterns are then measured and spectral and/or multivariate analysis is conducted on the resulting patterns. The present method here presented allows detection of components that by traditionally conventional method are difficult to detect. Furthermore the method and its device allow high-accuracy measurement of component characteristics and structure even at ultra-low concentrations. Structures, functions and changes of bio-molecules can be measured in real time.

DETAILED DESCRIPTION OF THE PREFERRED EMBODIMENT

Embodiment of the visible/near-infrared spectrometry and its device related to the present invention is described hereinafter with reference to FIG. 1 to 31.

In the visible/near-infrared spectrometry and its device related to the present invention, light in the continuous wavelength range 400 nm to 2500 nm or some part of the range (visible light and/or near-infrared light) is used to irradiate samples, using a commercial spectrometer (e.g. NIRSystem 6500 manufactured by Nireco Co.) and the subsequently acquired spectra of transmitted/reflected light are analyzed.

In such spectral analysis, reciprocals of light reflectance are logarithmically correlated to convert the detected spectra to the absorption spectra. Peaks in the resulting spectra are decomposed into element peaks by a spectrometric method. Multivariate analysis is then conducted on the element peaks, and attribution bands are obtained to build a model.

The water molecule is the smallest, and it should be the most active and mobile of all molecules. And practically all materials contain at least a small amount of water. So when a liquid sample (a water contained sample) specimen is irradiated with near-infrared light only specific wavelengths are absorbed by specific types of molecules present in the sample under scrutiny. Furthermore, absorbed wavelength changes vary according to the type of molecular structure. In the case of samples containing water molecules, the absorption phenomenon occurs in the wavelength range specific to the water molecule. The element peaks of water molecules shift as a result of interaction between that water molecule and the target component present in the sample specimen.

That means, that when a specimen sample is irradiated, light, that is, energy is absorbed differently by specific molecules according to specific wavelengths, and an energy level transits. Thus, specific wavelengths will produce discreet spectral patterns resulting from interaction between water molecules and specific target components, hydrogen-bonds and so forth.

The energy of a molecule is its vibration energy. As molecules are excited their vibration level shifts from the basic vibratory state to an excited state (transition of energy level). The basic vibration state is referred to as a fundamental tone. Transitions to second and third excited vibration states are referred to as overtone transitions. Transitions to excited states that are multiples of normal vibration states are referred to as a combination tones.

In the near-infrared wavelength range, many bands attributed to a functional group containing hydrogen (e.g. OH) exist and their overtones and combination tones also appear. That means, that near-infrared light irradiation of a sample specimen causes changes in the fundamental tone, the overtones and the combination tones according to specific wavelength ranges.

As mentioned above, overtones and combination tones are superimposed in the resulting spectral data obtained from near-infrared spectroscopy. The intensity of these overtones and combination tones is low and it decreases as overtone frequencies become higher multiples of the fundamental tone.

For this reason, the conventional near-infrared spectrometry requires spectral analysis of complex and superimposed low-intensity bands. Despite the large amount of information available, accurate measurement is traditionally difficult to achieve.

However, as it became possible to generate spectral pattern changes, in specific wavelength range, which can be measured later (invisible in terms of data) by giving intentional perturbations under predetermined conditions accurate measurements become feasible. Those predetermined conditions include intentional concentration level changes in step values, intentional consecutive light irradiations, intentional prolonged irradiations, intentional electromagnetic exposing, intentional light path-length changes, intentional temperature, pH, and pressure changes and so forth. Those changes induce the physical and chemical changes of the specimen sample. This means that the spectral response to these controlled changes produce spectral patterns specific to the subject component, and that multivariate analysis conducted on the acquired spectral data detects a response specific to each sample component. As a result detection and measurement of that specific sample component become possible.

As mentioned above, the near-infrared absorption spectra can be obtained by plotting the discreet absorbance (light absorbance rate) for specific wavelengths. Such quantitative analysis with near-infrared absorbance spectra requires a relational expression (calibration line) to relate the spectral data to an objective characteristic value (concentration or characteristic value). Generally, the calibration line can be obtained by measuring spectra of a sample whose objective characteristic value is known. That is achieved by performing preprocessing, including auto-scaling, smoothing, and first derivative operations on the obtained spectral data and subsequently analyzing those data with partial least square regression analysis (PLS). Furthermore, a highly accurate model can be build through cross-validation examination. And components are determined by principal component analysis (PCA) and further principal components are used to obtain inter-class distance by using SIMCA method for classification analysis.

For data analyses including the above mentioned preprocessing and multivariate analysis, the data processing software, Pirouette3.02 (which can be obtained from GL Science Inc.) was used.

Near-infrared spectrometry has low energy levels and as a result it does not damage the sample even by repeated irradiations to the same material. It is thus possible to conduct the repeated spectrometry while adding the predetermined conditions (giving perturbations). It was found that spectral responses changed dynamically when inducing the above mentioned perturbations. Due to those measurable dynamic changes, minimum variations in response spectra can be detected through spectral and/or multivariate analysis of those dynamic changes so that the detection and characteristics of components is now possible.

FIG. 1 is a block diagram illustrating the flow of visible/near-infrared spectrometry as related to the present invention. Spectra are measured while giving perturbations by adding predetermined conditions to the known sample 1. The obtained spectra are data-transformed and data-analyzed, and predetermined attribution bands of the sample are obtained while validating differences in absorption band intensity to build a model. Furthermore, the same perturbations are repeated on a different new sample 2, spectra are measured and compared to the data obtained from the first sample. Evaluation of the results is then used to build a model for a specific component.

FIG. 2 shows a characteristic portion of the proposed method. As shown, the proposed invented method is characterized by repeated spectral measurements conducted while simultaneously giving perturbations in the sample by performing, under predetermined conditions, concentration changes in the sample specimen. Spectral response patterns are the obtained based on data gathered from at least three times consecutive irradiations at specific wavelengths. Changes caused by the interaction of water molecules and target components are then detected and transitional spectral response patterns are then analyzed. As a result of such a method a qualitative model allowing identifying a component can be extrapolated and a quantitative model detecting the characteristics of a specific component can also be constructed. The models then provide information on the components present in the sample specimen.

FIG. 3 is a schematic diagram showing the characteristic portion of the device used in the present invention. As shown, visible/near-infrared spectrometry device 10 has a probe 12 comprising an optical means 12A capable of irradiating visible light and/or near-infrared light on a sample specimen S1 from a near-infrared generating device 11, a detecting device 12B to obtain spectra of transmitted light, reflected light, or transmitted/reflected light from the sample specimen S1. And said device 10 is arranged with a perturbations producing device 15 to giving perturbations by adding predetermined conditions to said sample specimen. A sample specimen environment adjusting device 14 and environmental conditions adjusting device including temperature, pH, and other changes, a data processing device 13 to conduct predetermined multivariate analysis on the obtained spectra, a control device 16 controlling perturbations in the sample, a perturbations producing device 15 and an operation timing of irradiating light and receiving light device.

The data processing device 13 performs multivariate analysis of the resulting spectra i.e. quantitative analysis to quantify the component characteristics using a PLS method and/or a cross-validation method or perform a qualitative analysis to determine classes using the PCA method and/or a SIMCA method. A model is then designed to measure distinctive properties of the respective components and/or component characteristics of unknown sample. Thereby components in sample specimen S1 can be detected and component characteristics can be measured.

Spectrometry in the wavelength range from 400 nm to 2500 nm is scanned at resolution of 2 nm using the above mentioned spectrograph, so that 1051 pieces of data can be obtained from a single scanning. It is thus possible to obtain 3153 items of data through three consecutive scanning. Processing those data allows identification of respective components as peaks corresponding to the interactions of water molecules with specific components are identified for different wavelength ranges.

FIG. 4 shows the intensity changes in the water molecule absorbance band. It shows the wavelength range where the intensity changes or shifts occur when the sample specimen comprising only water is consecutively illuminated every 15 minutes with wavelengths ranging from 400 nm to 2500 nm for 6 hours in a row. The responses occur and are shown in the blackened areas.

FIG. 5 shows a contour representing intensity changes (synchronous changes, that is, changes occurring simultaneously) in the water absorbance band ranging from 600 to 850 nm which are specific to the water molecules where changes in absorbance corresponding to the before-mentioned overtones and combination tones easily occur. Furthermore, FIG. 6 shows characteristic spectral peaks (peaks generated by positive correlation and peaks generated by negative correlation). It also shows that with respect to the peak at wavelength 606 nm, positive correlation peaks are simultaneously generated at the wavelengths between 640 nm and 738 nm. Negative correlation peaks are generated at a wavelength of 808 nm. These changes are induced by consecutive illuminations added to the sample specimen.

It is also found that some changes do not occur simultaneously but occur asynchronously following specific wavelength spectral changes. It is understood that in such specific wavelength ranges information concerning water absorbance band can be correlated to other complex changes observed at specific wavelengths.

For this reason, a response of the predetermined water molecule element peak generated when the spectrometry is conducted on the specific sample specimen shows that a change occurs in the specific wavelength range according to the component present in the sample specimen. The degree of this change is not directly determined by the resulting spectral data but can be obtained from data processing and multivariate analysis of the spectra.

Furthermore, it is observed that even by scanning with sample component concentration changes in step values, by scanning with light path-length changes, and by scanning with added external conditions such as variable temperature and pH conditions, there is a slight difference in the response between the first and second scanning, or between the second and third scanning, so that differences between the responses in element peaks of water molecules depending on respective sample components can be found.

Therefore, said perturbations are intentional condition changes to generate dynamic changes to the spectral responses by conducting several times of irradiations at time intervals for spectral measurement. In the present invention, these perturbations are referred to as WAPOT (Water Activating Perturbations Over the Time).

Scanning is thus conducted while giving water activating perturbations (WAP) by inducing physical and chemical alterations through concentration changes, repeated irradiations, irradiation time extensions, electromagnetic applications, path-length changes, temperature changes, pH changes, pressure changes and so forth. Responses to discreet components present in the respective samples and their corresponding spectral responses (intentional changes of spectral pattern including predetermined water molecule element peaks) can then be detected.

The measurement result of each sample is described herein after.

Embodiment 1

Embodiment 1 is an example of determination between bacteria, CNS (coagulase-negative *staphylococcus*) and CPS (coagulase-positive *staphylococcus*) in sample specimen, and measurement of their respective concentrations.

Sample specimens in which respective bacteria are mixed in BPW (buffer peptone water) are prepared and those sample specimens are then injected in a silica cell of 1 mm.

The samples are prepared in such a way that respective referential concentrations of CFU (colony forming unit) are changed by tenfold steps, that is, in range from $10^{-1}$ to $10^{-10}$ The prepared samples are consecutively irradiated three times with light in the wavelength range from 400 nm to 2500 nm and spectrometry is then measured at 2 nm intervals.

When determining the presence of respective bacteria in the sample specimens could be performed in buffer peptone water solution, cow's milk or could be measured bacteria cultured in a Petri dish.

The spectrograph used here is a near-infrared spectrograph (NIRSystem 6500 manufactured by Nireco Co.) and the measurement temperature is a constant at 37° C.

FIG. 7 shows the measured absorption spectra. The shaded portion is excluded from the data and is considered noise. The obtained data are then preprocessed by auto-scaling, smoothing processing, and first derivative processing using the data-processing software, Pirouette3.02 (which can be obtained from the GL Science Co.) The data-processing software transforms the data which is then used to measure respective bacteria concentration by PLS and cross-validation analysis according to the model. Bacteria in the respective sample specimens are also identified by their principal component analysis (PCA) and SIMCA analysis.

FIG. 8 shows a regression vector for CNS concentration obtained as a result of PLS analysis. FIG. 9 shows a CPS concentration regression vector. Important wavelengths for which clear responses are obtained are 1406 to 1500 nm, 1180 nm, and 1306 nm for CNS, and 740 nm, 770 nm, 808 nm, 1156 to 1198 nm, 1466 nm, 1476 nm, 1650 nm, 1686 nm, 1704 nm, 1720 nm, 1750 nm, 1846 nm, and 1890 nm for CPS. Furthermore, FIG. 10 shows a calibration line for CNS concentration and FIG. 11 shows a calibration line of CPS concentration.

In FIG. 10 and FIG. 11, the X-axis (horizontal axis) represents measurement values (reference values obtained by the conventional method by diluting known sample specimen) and Y-axis (vertical axis) represents probable values obtained from the constructed model derived from spectral and multi-variate analysis.

CN^6-2 in FIG. 10 indicates the 2nd scanning data of the sample specimen at the 6th level when CNS concentration is diluted by tenfold increments from $10^{-1}$ to $10^{-10}$. CP^6-3 in FIG. 11 indicates the third scanning data of the sample specimen at the 6th level in the tenfold dilution levels of CPS concentration.

Numeric values on the horizontal axis in FIG. 10 express natural logarithmic scales of CNS concentration. For example, undiluted CNS solution of $1.12 \times 10^8$ CFU/ml concentration is used as a reference sample and measurement is conducted with 10-level samples which are diluted into 10 of tenfold increments. That means, in $(1.12 \times 10^8) = 18.53$ is a reference concentration (CNgen-2etc. in FIG. 10). The first one diluted from this 10 fold increments is expressed by CN^10=ln($1.12 \times 10^7$)=16.23. And the one further diluted by a factor of 10 is CN^9=ln($1.12 \times 10^6$)=13.93.

FIG. 11 shows the result of measuring samples whose concentration are diluted by a successive a factor of 10 when a CPS of $1.05 \times 10^8$ CFU/ml concentration is used as a reference stock solution. FIGS. 10 and 11 show that it possible to obtain a calibration line with which CNS and CPS can be measured in a concentration range from $10^{-1}$ to $10^{-10}$ and particularly for CPS which are bacteria harmful to the human body. Ultra-low concentration samples in which the concentrations are diluted to $1.05 \times 10^8 \times 10^{-10}$ CFU/ml can be accurately be measured.

FIG. 12 shows a cross-validation analysis result and expresses the result of validation error SEV, and validation correlation rVal, etc. Based on those results, for example, with respect to Factor 6 of the CPS calibration line, the cumulative contribution rate (cumulative) is 97.56091% and the validation error SEV is 3.096218. The correlation coefficient is rVal=0.944926. It is thus clear that a highly accurate calibration line can be obtained.

Furthermore, said CNS and CPS were determined using samples in which concentration of mixtures containing CNS and CPS were diluted in step values (successive a factor of 10). Using 2nd and 3rd measurement data among spectra which are measured three times on each respective sample, principal component analysis (PCA) is then conducted on a group of samples. FIG. 13 shows a three-dimensional plot which is based on the 1st principal component (Factor 1), the 3rd principal component (Factor 3) and the 5th principal component (Factor 5) which were obtained by said PCA. As shown in FIG. 13, the visible/near-infrared spectrometry method proposed by the present invention, clearly separates clusters of CNS and CPS by a boundary L1. It means that the present invention achieves easy distinction between CNS and CPS which has been impossible to achieve through visible/near-infrared spectrometry.

FIG. 14(a) shows the result of SIMCA analysis when respective pre-processes and conversion processes are changed. In measurement conditions A1 to A6, "WATER EXCLUDE" means water molecule spectra excluded from analysis, "BPW" means using buffer peptone water BPW, "DILUTED SAMPLE" means the use of a sample prepared in such a way that the concentration is previously diluted to each predetermined value, "NOISE EXCLUDE" means followed by the processes of noise exclusive, and "3 TIMES" means three consecutive irradiations, respectively.

"Auto-scaling", "smoothing" (15), and "1st Derivative" (25) respectively mean "auto-scaling process" and "the smoothing process" with a smoothing window of 15 nm, and a 1st derivative process conducted with a smoothing window of 25 nm.

That is to say that in the measurement condition A6 in which water spectra is removed from the data, buffer peptone water is used. The sample in which the concentration is previously diluted by step values, noise is subjected to noise removal treatment, and three times consecutive irradiations are conducted. When SIMCA analysis is performed on CNS and CPS through data processing, including the auto-scaling processes, the smoothing process window is 15 nm, and the 1st derivative (every 25 nm). The interclass distance between CNS and CPS is 4.254.

When comparing A4 and A8, two different results for interclass distances have been obtained depending on what samples have been used to build up the models. The interclass distance for A4 is 1.156 while the interclass distance in the case of not adding the same samples further diluted with water at various concentrations to the samples obtained by serial dilution with peptone buffer solution is 4.132, which shows that the determination power is increased. As for obtaining the various concentrations, there are two methods. In the first method, the concentration of each sample is set at a predetermined original value which is being prepared by addition of predetermined amount of water and/or buffer peptone water to an undiluted sample (henceforth referred to as single or serial pre-addition dilution). In the second method, the undiluted stock solution is measured as a sample and, after the completion of the measurement; water and/or buffer peptone water are added to dilute the concentration (herein after referred to as multiple and post-addition dilution). In this process, bacteria can be detected by using pre-addition dilution to extremely low concentration levels. Furthermore, in comparing A8 and A6, differences are observed according to whether irradiation is conducted one time or three times. The interclass distance of A6 after three times irradiations is 4.254 and it also shows that the determination power is increased.

Generally, an interclass distance of no less than 3 is considered significant for class determination. The above mentioned resulting interclass distance of 4.254 shows that the SIMCA model allows significant differentiation between CNS and CPS FIG. 14(b) shows the result of a determination process using SIMCA. For example, with respect to CNS, all 34 determinations were successful and no determination errors occurred. And again, with respect to CPS, all 36 determinations were successful and no determination errors occurred. It clearly shows that the determination process is highly reliable.

As mentioned above, it becomes possible to build highly reliable models to determine the presence of bacteria CNS (coagulase negative staphylococcal) and CPS (coagulase positive staphylococcal) in sample specimens through the use of spectrometry combined with condition changes in the sample specimen (that is, WAP perturbations) and three consecutive irradiations. Dilution of the concentration level must be performed by a factor of 10 in a wide range from $10^{-1}$ to $10^{-10}$ (pre-addition dilution).

Therefore, the visible/near-infrared spectrometry related to the present invention ensures detection of bacteria that are harmful to the human body but are difficult to detect.

The present invention does not require the use of bacteria-cultures and enables detection by real time-measurement, while the conventional culture method requires about 48 hours.

Embodiment 2

Embodiment 2 is an example of the detection of "prion" protein PrP containing no metal component and prion proteins PrP (CU) and PrP(Mn) which have a metal component. In this embodiment, a spectrometry is conducted with light in the wavelength range from 400 nm to 2500 nm, light irradiation is added in succession every 15 minutes as a perturbation for a six hours and multivariate analysis is conducted by the PCA method and the SIMCA method.

A samples of PrP prion protein alone and a sample PrP (Cu) containing copper in its molecular structure, as well as a sample of PrP(Mn) containing manganese in the its molecular structure are prepared. Then multiple samples of prion solutions at different concentration levels are also prepared (single and pre-addition dilution). The respective dilution levels are 1 mg/ml, 0.5 mg/ml, 0.1 mg/ml, 0.05 mg/ml. Spectrometry is then conducted on the respective prion solutions.

Multivariate analysis is then conducted to obtain the spectra of the 1st principal component (Factor 1), 3rd principal component (Factor 3) and 5th principal component (Factor 5). FIG. 15 shows a determination result based on the obtained principal components and loadings.

FIG. 15(a) shows the determination result of PrP, PrP (CU), and PrP(Mn) with the 1st principal component (Factor 1) and the 3rd principal component (Factor 3). FIG. 15(b) shows the determination result of PrP, PrP (CU), and PrP (Mn) with the 3rd principal component (Factor 3) and the 5th principal component (Factor5). FIG. 15(c) shows loadings of respective principal components.

FIG. 15(a) clearly shows that PrP, PrP(Cu), PrP(Mn) are well determined. However, PrP1 is separated from a PrP group circled with a wavy line, Cu1 from a PrP (Cu) group, and Mn1 from a PrP (Mn) group, and said PrP1, Cu1 and Mn1 are data obtained after the first irradiation. This shows that accurate determination can not be expected from a single irradiation but that models for group determination can be obtained by repeated measurements while giving perturbations (WAP).

FIGS. 15 (a) (b) show that it is possible to build models when spectra analysis is conducted while changing condition that include the dilution change in step values of sample concentration and consecutive light irradiation every 15 minutes while giving perturbations (WAP), to determine Prion proteins PrP, PrP (Cu), and PrP(Mn).

In FIG. 15(c), the 1st principal component (Factor 1), obtained at a wavelength of 1466 nm, provides the basis for a line PC1, which shows the loading of the 1st principal component (Factor 1) Wavelengths of 1340 nm and 1424 nm are the basis for line PC3, showing the loading of the 3rd principal component (Factor 3) and wavelengths of 1364 nm, 1394 nm and 1476 nm are the basis for line PC5 showing the loading of the 5th principal component (Factor 5).

FIG. 16 shows the result of interclass distance measurement by SIMCA analysis. FIG. 16 shows that the distance between PrP (Cu) and PrP(Mn) is 28.81, and that the distance between PrP(Cu) and Prp is 4.15. Because the distance longer than 3 is adequate for class determination as mentioned before. Prion proteins can be clearly detected and identified by the present method.

That means, that spectrometry conducted while giving perturbations (WAP) followed by repeated irradiations at time intervals (every 15 minutes) permit the detection of proteins containing metal components such as PrP (Cu) and PrP (Mn). As a result, it is now possible to conceive models which can accurately determine whether prion proteins PrP and prion protein PrP(Cu) are present. Prion protein PrP(Cu) are thought to be related to mad cow disease (BSE: bovine spongiform encephalopathy).

FIG. 17 shows a result of interclass distance measurement by the SIMCA processing conducted on another sample on which irradiations were repeated 26 times every 15 minutes for 6 hours. As shown in FIG. 17, the interclass distance increases to some extent with increasing irradiations numbers. That means that determination accuracy rate also increases accordingly.

For example, the interclass distance between PrP(Cu) and PrP(Mn) which is 5.6 after 3 irradiations increases to 25.8 after 20 irradiations. However, the interclass distance between PrP(Cu) and PrP reaches its maximum after 11 irradiations and thus follows a different pattern. It means that optimal numbers of irradiations for specific perturbations and specific components do exist.

Even in prion protein having similar structures, response changes occur according to component differences when they are subjected to perturbations. It means that response changes depend on the bio-molecular structures, function differences and their variations under given perturbations. Therefore, bio-molecular structures and functions can be detected by analyzing their response to specific perturbations.

FIG. 18 shows the result of interclass distance measurement based on respective sample concentrations where specific prion protein PrP without metal component and a prion protein PrP(Cu) containing metal components are present in a solution where, PrPinW(Cu) is added to PrP in the water solution. Multiple samples are prepared by mixing respective predetermined stock solutions with buffer water and the respective sample concentrations are changed to 1 mg/ml, 0.5 mg/ml, 0.1 mg/ml, 0.05 mg/ml (previous addition to the sample). Interclass distances are then measured for those samples.

For example, the interclass distances between PrP (Cu) and PrP are 0.861595 at a concentration of 1 mg/ml, 2.434433 at a concentration of 0.5 mg/ml, 2.674994 at a concentration of 0.1 mg/ml, and 7.862999 at a concentration of 0.05 mg/ml. The interclass distance subjected measurement increases as concentration levels decrease; determination of component is then possible because the interclass distance is superior to 3 which is the minimum for class determination, as described earlier.

Based on the above-mentioned experimental result, using the spectrometry method described here above, it is found that determination rate increases as sample specimen concentrations decreases in wide range concentration dilutions by pre-addition dilution.

Embodiment 3

Embodiment 3 is an example of determination among prion proteins PrP without metal component and a sample specimen PrP(CU) containing copper as PrP(metal) with metal component. The determination is obtained by changing light path-length from 1 mm to 4 mm. In this embodiment, spectrometry is conducted with light in a wavelength range of 400 nm to 2500 nm. Light is irradiated for 48 hours and light irradiation is repeated every 6 hours. Multivariate analysis is then conducted by the PCA method and the SIMCA method. PrPinW(Cu) to which metal component Cu is added in the PrP water solution is then measured to determine how the change affects the measurement results.

FIG. 19 shows the results obtained when using loadings of the 3rd principal component (Factor 3) and the 9th principal component (Factor 9). FIG. 20(a) shows the results of SIMCA analysis. FIG. 20(b) shows interclass distances as determined by SIMCA and FIG. 20(c) shows the determination results.

Based on FIG. 20(a), it is found that classes of PrP and PrP(Cu) can be clearly determined when they are measured with different light path-lengths. PrP(Cu) and PrPinW(Cu) can clearly be identified by that method. Based on FIG. 20(b), the interclass distance between PrP(Cu) and PrPinW(Cu) is 24.84 and is clearly defined. Although the interclass distance between PrP and PrP(Cu) of 1.19 which is small, there is no problem because the determination error based on the results shown in FIG. 20(c) is zero.

As mentioned above, it is found that determination between the prion protein PrP and the prion protein PrP(Cu) containing a metal component can be realized through spectrometry using different light path-lengths. However, FIG. 20(a), shows that there is no difference between PrPinW (Cu) when changing light path-length. That means, that in the sample specimen in which only a metal component Cu has been added to the PrP water solution, pattern changes do not occur in the response spectra even when spectrometry is conducted with different light path-lengths and an interaction between a water molecule and a target component does not occur either in such a case. However, in the experiment using visible/near-infrared spectrometry, the prion protein PrP (metal) containing metal component in its molecular structure can be identified. This type of spectrometry is thus considered effective.

Detection and distinction between prion proteins PrP with no metal component and prion proteins PrP (metal) with metal component is achieved by giving specific perturbations such as light path-length changes (1 mm and 4 mm respectively).

Embodiment 4

Embodiment 4 is an example of determination between prion proteins PrP without metal component and prion proteins PrP (CU) with a metal component. PrPinW (Cu) is obtained by adding a metal component Cu to a water solution of PrP, and the determination is conducted by changing temperature (respectively 21° C., 30° C., 35° C., 37° C.). Spectrometry is then conducted on the respective prion water solutions in which concentrations levels are previously changed at 4 distinct levels. That is, 1 mg/ml, 0.5 mg/ml, 0.1 mg/ml, 0.05 mg/ml (pre-addition dilution).

Spectral data is then obtained by conducting spectrometry on the respective concentration sample specimens at the formerly described 4 levels. That means that each predetermined concentration sample produces 4 pieces of spectral data. A principal component analysis is thus conducted on 4 pieces of spectral data which are obtained when adding temperature changes and applying SIMCA to the data produced by the perturbations in the sample specimens at different concentration levels.

FIG. 21 is a three-dimensional graph showing SIMCA distances. This shows that SIMCA distance is the highest when the sample specimen concentration 0.05 mg/ml is the lowest. Respective SIMCA distances are no less than 5, which is well above the minimum needed for class determination.

It is also clear that SIMCA-distance patterns change depending on the respective specimen components. That means, it is shown that when temperature changes are given as perturbations, responses change according on respective specimen components and differences occur depending on specimen component structures and functions. Thus, temperature change sample specimens can be perturbations which dynamically changes response spectral patterns.

Embodiment 5

Embodiment 5 is an example of measuring antigen concentrations in sample specimens. Anti-bisphenol A scFv is used as an antibody and Bisphenol A is used as an antigen. Diluted sample specimens where respective concentrations are gradually diluted in step values in the buffer water (PBS buffer) are injected in a silica cell at a light path-length of 1 mm, and in wavelength range of 400 nm to 2500 nm. Samples are then subjected to at least 3 consecutive irradiations for spectrometry.

Said antibody sample concentrations are established in 4 levels, that is, 10 ng/ml, 100 ng/ml, 1 μg/ml, 10 μg/ml. Antigen samples whose concentrations are established in 6 levels from 1 pg/ml to 100 ng/ml. There are 32 mixture samples, that is, 2 units for 16 types of mixture samples. And spectrometry is then conducted on these samples, and adding respective single samples (10 types, 22 samples), one sample containing only water (1 sample), and on sample containing only buffer water (3 samples), totally 58 samples.

Noise processing, smoothing processing, and an auto-scaling processing are conducted on the obtained spectral data and then PLS followed by cross-validation analysis.

FIG. 22 shows an analysis result. FIG. 22(a) shows a calibration line. The horizontal axis represents Measured Y which is a measurement value by a conventional method and the vertical axis represents PredVal which is a predicted value obtained by the visible/near-infrared spectrometry in the present invention. Based on those results, antigen concentration is found measurable up to 1 ppt (one trillionth).

FIG. 22(b) shows validation errors SEV which are obtained through cross-validation analysis. After the 1st irradiation, a cumulative contribution rate (cumulative) of Factor 5 is 99.94188% and the validation error SEV is 3.558607. However, after repeating irradiation three times, a cumulative error of Factor 9 is 99.94567% and the validation error SEV becomes 1.008785.

It is found that the validation error SEV becomes one third after giving perturbations (WAP) multiple times such as performing 3 consecutive irradiations. Antigen concentration in the sample specimen can be measured with and accuracy 3 times superior to that obtain through the conventional method.

FIG. 22(c) shows interclass distances obtained by SIMCA processing. As shown, that distance is 8.65 after the 1st irradiation then becomes 9.79 after the 2nd irradiation (1 & 2), and as irradiation is repeated three times (1 & 2 & 3), the numerical value increases to 10.11. That means, multiple irradiations provide highly accurate determination of antigen components.

Embodiment 6

Embodiment 6 is an example of measuring the diameter of granule to be dissolved in sample specimens, before dissolution. In this embodiment, coffee granule diameters are measured before dissolution. Coffee granules are gradually refined through grinding times extending from 0 seconds, 20 seconds, 60 seconds, to 90 seconds when instant coffee is ground with a mixer. Samples whose concentrations are serially changed (pre-addition dilution) to 4%, 3%, 1% are injected in a silica cell. The silica cell is then irradiated 3 consecutive times with light in the wavelength range of 400 nm to 2500 nm and a light path-length of 1 mm.

Noise processing, smoothing processing (17 points, every 34 nm), as well as auto-scaling are conducted on the obtained spectral data and then PLS and cross-validation analysis are conducted to build up a regression model.

FIG. 23 shows an analysis result. In FIG. 23(a), the horizontal axis Measured Y represents measurement values by the conventional method and the vertical axis Pred Cal represents probable values obtained by the visible/near-infrared spectrometry according to the present invention. Said measurement value Y is not the value obtained by actually measuring the coffee granule diameter but expressed as a logarithm of grinding time. This is because the granule diameter is assumed to become smaller as grinding time is increased (that is, becomes longer). Thus, it is found that the present invention enables obtainment of building models to assume coffee granule diameter before dissolution.

FIG. 23(b) shows validation errors SEV obtained through cross-validation analysis. As shown, the cumulative contribution rate, Factor 5, at the 1st irradiation, is 98.31849% and the validation error SEV at that moment is 0.937039. However, after the 3rd irradiation, the cumulative contribution rate, Factor 6, becomes 99.8904% and the validation error SEV obtained through cross-validation analysis is now 0.466675.

That means with the spectrometry obtained by 3 consecutive irradiations as perturbation (WAP), coffee granule diameter before dissolution, can be measured at double the accuracy rate compared to the spectrometry is performed with only one irradiation.

When the sample specimen concentrations are changed, they are measured by SIMCA which is a qualitative analysis for the said class determination how to affect a difference of granule diameter before dissolution, that is, a determination distance (SIMCA DISTANCE) between a granule state and a powder state.

FIG. 24(a) shows SIMCA distances which are measured in respective specimen concentrations when the granule state and the powder state of coffee are determined. FIG. 24(b) shows SIMCA distances which are measured by respective specimen concentrations when the granule state and the powder state of sugar are determined. FIG. 24(C) shows relative coefficient (Rv) and validation error (SEV) when the PLS analysis and the cross-validation analysis are conducted on the granule and the powder state of sugar.

As shown in FIG. 24(a), the SIMCA distances are no less than 5 at any level of concentration from 1 to 4% which means that the granule state and the powder state of coffee can be sufficiently determined. That is particularly true when the concentration is diluted to 1%, the SIMCA distance is then 15.96 which is a maximum and thus the determination power is then at its highest level (maximum)

As shown in FIG. 24(b), when the granule state and the powder state of sugar are determined, the SIMCA distance is 1.59 at a specimen concentration of 4%, and the value is then too small to allow determination. However, if the concentration level is halved to 2%, the value becomes sufficient for determination. Thus, it is found that optimal specimen concentration changes vary according to specific components. That means that response changes occur when giving perturbations and changing concentration levels in the specimen and that those changes generate differences depending on component structures and functions of said components.

Based on FIG. 24(c), with respect to the correlation coefficient of the regression model for sugar measurement, granule state is 0.995 and powder state is 0.9998, which shows that granule size can be measured with high correlation.

It is thus evident that the use of visible/near-infrared spectrometry, as described in the present embodiment, allows determination of coffee granule diameters and sugar granule diameters to a high degree of accuracy.

Embodiment 7

Embodiment 7 shows an example of determination between bacteria of different types present in a sample specimen. Bacteria, *staphylococcus* (msta) and *Streptococcus* (mstr) found in cow-milk are gradually diluted (with a PBS buffer solution) into concentrations going from $10^{-1}$ to $10^{16}$ (colony/ml). 76 discreet samples are prepared and injected into a silica cell with a light path-length of 1 mm. The different samples are then subjected to 3 consecutive irradiations with light in the wavelength range from 400 nm to 2500 nm. The spectra of those irradiations are then analyzed.

Based on the obtained spectral data, a principal component analysis (PCA) and a SIMCA analysis, which are similar to the above-mentioned analysis methods, are then conducted.

FIG. 25 shows the result of such analyses. Based on the result of determination between msta and mstr in the 1st principal component (Factor 1), the 2nd principal component (Factor 2) and the 3rd principal component (Factor 3), the bacteria belonging to the msta group are clearly discriminated from the bacteria belonging to the mstr group.

Thus, it is found that using spectrometry while giving perturbations (WAP) and performing said spectrometry multiple consecutive times (3 times), bacteria belonging to the msta group and bacteria belonging to the mstr group, both of which are found in cow milk, can clearly be differentiated. That means, that visible/near-infrared spectrometry performed according to the present invention requires no culture time and allows determination of different types of bacteria in real time, while the conventional culture methods require about 48 hours before the results of the culture can be obtained.

Embodiment 8

Embodiment 8 is an example of measuring component concentrations in blood plasma, rumen juice, cow and other mammals' milk. Using raw biological fluids, sample specimens are injected into a silica cell giving a light path-length of 1 mm and are then subjected and analyzed through spectrometry with light in the wavelength range from 400 nm to 2500 nm. In such a measurement procedure, spectrometry is conducted twice a day (once in the morning and once in the evening) for 3 consecutive days. Furthermore, after changing cow feeds for 3 weeks, a similar spectrometry is again conducted twice a day (once in the morning and once in the evening) for 3 consecutive days to confirm the effects.

In the above case, the measurement is conducted once in the morning and once in the evening for consecutive 3 days. However measurement may be conducted more than twice a day or for more than 3 consecutive days. Spectral data obtained as mentioned above, are pre-processed and analyzed by the PLS method and the cross-validation method.

FIGS. 26 and 27 show the results of such analysis. FIG. 26(a) and (b) show the results obtained for several components assumed to be present in cow milk(Fat, Crude Protein, Casein, True protein and milk urea nitrogen: MUN, Lactose), at different concentration levels, through measurements taken from a cow's blood plasma spectra. FIGS. 26(c) and (d) show results obtained several blood plasma components assumed to be present in blood plasma(Albumin, Glucose, Blood urea nitrogen: BUN)through measurements taken from cow milk spectra instead.

And FIGS. 27(a) and (b) show the results of measurements of assumed cow milk components (Fat, Crude Protein, Casein, True protein, MUN, Lactose), at different concentration levels, based on measurements taken from cow's rumen juice spectra. FIGS. 27(c) and (d) show the results of measurements obtained for assumed rumen juice components (pH, ammonia nitrogen: NH3-N, Fat acid C2, Fat acid C3, Fat acid C4) at different concentrations levels, based on measurements of cow milk spectra.

As shown in FIG. 26(b) through the use of visible/near-infrared spectrometry, as described in the present invention, the concentrations of raw cow milk components can strongly be inferred from and correlated with measurements taken from the spectra of cow blood plasma. In particular, the correlation coefficient R=0.938 with respect to casein falls into a statistical significance p<0.001 and this is with an assumption error occurring at 1/1000. Thus and as shown in FIG. 27(b), Casein concentration contained in raw milk: R=0.902 can be assumed at P<0.001 by measuring cow Rumen juice spectra.

Thus, spectrometry performed while giving perturbations (WAP), changing time intervals between measurements, changing measurement frequency and changing component concentration in raw milk taken from mammals such as cows allows precise measurements on biological fluids, including blood plasma and rumen juices taken from such mammals. Cross evaluations between blood plasma, rumen juice and raw milk can thus be assumed based on those measurements. That is, measurements taken from raw milk make it easy to infer component concentrations in both blood plasma and rumen juices and vice-versa, thereby biological information of milch cows can be obtained easily.

Embodiment 9

Embodiment 9 is an example of measuring a plurality of component concentrations present in cow milk while giving perturbations combined with a plurality of measurements with different light path-lengths. Sample specimens injected in silica cells are analyzed by spectrometry in the first wavelength range from 700 nm to 1100 nm and the second wavelength range from 1100 nm to 2400 nm.

As long as the near-infrared light is, specifically, in the wavelength range of 700 nm to 1100 nm, even the near-infrared light has a transmission power of 10 to 100 times of that of long wave wavelength. And the light path-length may be 1 to 2 cm with the near-infrared light in shortwave wavelength. Reasonable-price containers such as test tubes and the like may be used as substitutes for special silica cells.

Therefore, using sample specimens injected in silica cells or test tubes in light path-length of 1 mm, 4 mm, and 10 mm, the spectrometry can be conducted in shortwave wavelength range 700 nm to 1100 nm.

After a sample specimen is injected in a silica cell 3 shown in FIG. 28(a) having a rectangular sample injecting unit 3A with a width of 1 mm, predetermined light are irradiated in directions 4 and 5 shown in FIG. 28(b) to set arbitrary light path-lengths. By this way, light path-length of the same sample specimen is changed to 1 mm, 4 mm, and 10 mm and sample specimens are measured with these different light path-length. This shows that as a light path-length increases, noise decreases and accuracy increases.

The obtained spectra is analyzed by the PLS method and the cross-validation to obtain SECV (cross-validation error) which are shown in FIGS. 29(a), (b) and (c).

FIG. 29(a) shows SECV in the measurement of FAT (fat concentration in the cow milk), FIG. 29(b) shows SECV in the measurement of PROTEIN (protein concentration in the cow milk), and FIG. 29(c) shows SECV in the measurement of LACTOSE (lactose concentration in the cow milk).

Based on the result of Fat measurement as shown in FIG. 29(a), SECV at the wavelength range 700 nm to 1100 nm is 0.45 with respect to the light path-length of 1 mm, while SECV in the wavelength range 700 nm to 1100 nm with respect to the light path-length of 4 mm and 10 mm is 0.2. Therefore, it is found that accuracy measurements can be assured by increasing the light path-length in the short wavelength range 700 to 1100 nm.

FIG. 29(c) shows a result of the lactose measurement, where SECVs at shortwave wavelength of 700 nm to 1100 nm and at long wavelength of 1100 nm to 2400 nm are both 0.09. Therefore, highly accurate measurement can be assured in the shortwave wavelength of 700 nm to 1100 nm.

As mentioned above, because samples can be measured in shortwave wavelength range and with long light path-length, the determination with low noise and small error can be realized and ordinary test tubes may be used instead of special silica cells.

It is also clear that highly accurate models can be obtained by measuring a variety of data with different light path-lengths.

Embodiment 10

Embodiment 10 is an example of measuring fat concentration in the cow milk, where a sample specimen is injected in a silica cell of light path-length 1 mm and light in wavelength range 500 nm to 1000 nm is consecutively irradiated three times to conduct the spectrometry while applying voltage 10V as a perturbation (WAP).

The spectrometry is conducted by consecutively irradiating lights in the wavelength range 500 nm to 1000 nm three times using the spectroscope manufactured by the Kubota Co. while applying voltage of 10V using the "Milk Checker" (manufactured by the Oriental Instrument Co.) for measuring electric conductivity of cow milk as a voltage applying means. As for a spectrometer, the other spectroscope (e.g.

near-infrared spectroscope NIRSystem6500 manufactured by the Nireco Co.) may be used and it is not specifically limited to these.

FIG. 30 shows the analysis where the obtained spectra are analyzed by a PLS method and cross-validation. FIG. 30 (a) shows analyzed a regression vector and FIG. 30(b) shows results of the analysis.

FIG. 30(a) shows that the validation correlation (rVal) of Factor 10 when applying no voltage (Without EMF) is 0.98, and the validation error (SEV) at that moment is 0.204269. Factor 9 after applying voltage (After Applying EMF) reads rVal=0.996256 and SEV=0.087212. With the measurement while applying voltage (In the presence of EMF), Factor 9 reads rVal=0.997483 and SEV=0.071528.

That means, when the spectrometry is conducted while applying 10V voltage as a perturbation (WAP), the validation error becomes one third, therefore it is found that models having three times accuracy can be obtained.

As explained in the above-mentioned Embodiments 1 to 10, in the spectrometry method for measuring component characteristics in respective samples using light in the wavelength range of 400 nm to 2500 nm, the spectrometry is conducted while giving water activating perturbations (WAP) to activate water existing within and/or around sample specimen by adding predetermined conditions to said sample specimen, and predetermined patterns of response spectra changing depending on respective components of said sample specimen are measured and analyzed by a spectral and/or a multivariate analysis, thereby enabling identification that has been difficult by the conventional methods and highly accurate measurements of component characteristics. And further detection of ultra-low concentration components and identification of components and/or real-time measurement of component characteristics can be realized.

Further, the spectrometry method of the present invention has optimal prescribed perturbations (WAP) for identifying predetermining specimen components based on specimen components to be measured. The prescribed spectrometry conducted while giving that prescribed predetermined perturbations enables easy measurement of predetermined specimen components.

As mentioned above, the perturbations in the present invention are condition changes to induce physical or chemical changes in sample specimens, and they include repeated light irradiations, changes of sample specimen concentration, extension of irradiation time, electromagnetic force applications, light path-length changes, temperature changes, pH changes and pressure changes. Besides, changes of feed for cows shown in Embodiment 8 are also included. Further, the physical or chemical changes induced in the sample specimen may be adding vibration, sound waves, and pressure.

With regard to a simple type visible/near-infrared spectrometry device, a spectrometry device which can conduct the spectrometry by irradiating some specific wavelengths (Important wavelengths) satisfies the requirement because lights in the specific wavelengths (Important wavelengths) are important for determining or measuring the specific components of the sample specimens as mentioned above. Therefore, a visible/near-infrared spectrometry device 20 shown in FIG. 31 can be a simple device that provides the necessary functions needed for determining a specific component.

Said visible/near-infrared spectrometry device 20 comprises a perturbation giving means 22 for giving perturbations by adding predetermined conditions to sample specimen S2 contained in a sample specimen containing unit 21; an optical means 23 for irradiating said sample specimen S2 with visible light and/or near-infrared light in the wavelength range of 400 nm to 2500 nm or a part of that range and in specific wavelength ranges which are predetermined for that specific sample specimen S2; a detecting means 24 for obtaining spectra of transmitted light, reflected light, or transmitted/reflected light from said sample specimen S2; and a data processing means 25 installed with a processing soft for performing predetermined spectral and/or multivariate analysis on the obtained spectra. Further the device may comprise a displaying means 26 for display a determination result which distinguished the measurement result.

With the visible/near-infrared spectrometry device 20 of the above-mentioned construction, the spectrometry can be conducted by irradiating light in the specific wavelengths (Important wavelength) which are appropriate to determine respective components and/or to measure the component characteristics, so that respective specific components can be easily estimated in short time. Furthermore, the visible/near-infrared spectrometry device 20 is constructed in such a way that simple determination and simple measurement of specific components can be realized by building up models to make it possible to determine respective components and/or to measure component characteristics.

DESCRIPTION OF DRAWINGS

[FIG. 3]
A schematic diagram showing the characteristic portion of the present invention device

[FIG. 6]
A chart showing synchronous changes of wavelengths

[FIG. 12]
A diagram showing an calibration result of a cross-validation analysis

[FIG. 14]
(a) A diagram showing a result of SIMCA analysis which seeks a interclass distance between CNS and CPS (b) A diagram showing a SIMCA determination result

(a) A diagram showing a determination result of PrP, PrP(CU), and PrP(Mn) with the 1st principal component (Factor 1) and the 3rd principal component (Factor 3), (b) A diagram showing a determination result with the 3rd principal component (Factor 3) and the 5th principal component (Factor 5), (c) A diagram showing loadings of respective principal components

[FIG. 16]
A diagram showing SMICA interclass distance among PrP, PrP (Cu), and PrP(Mn)

Figure 1:
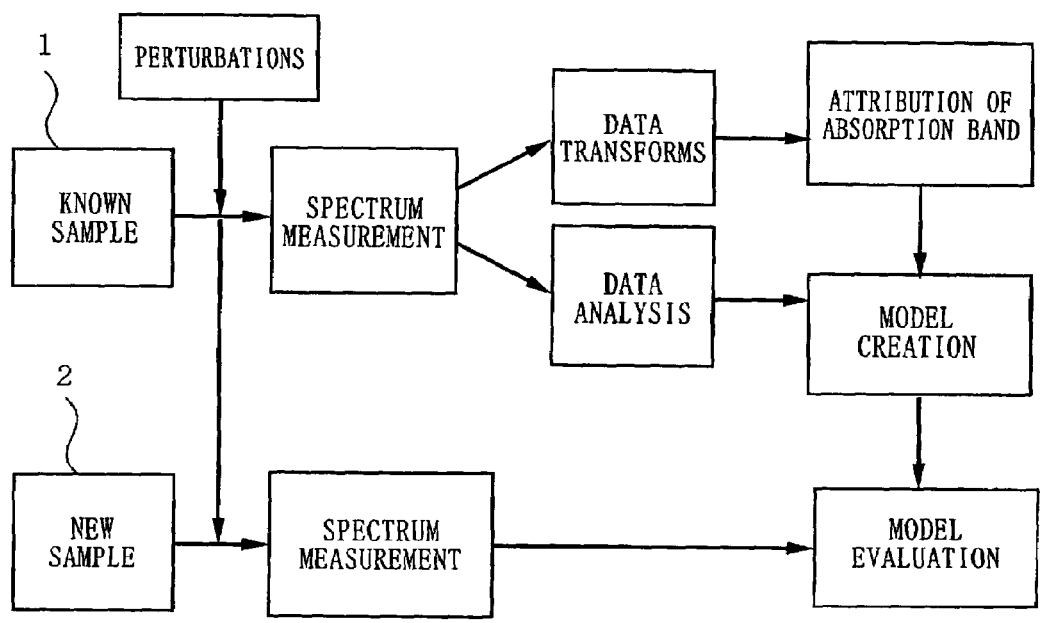
[FIG. 1]
A block diagram showing flow of a visible/near-infrared spectrometry related to the present invention
Figure 2:
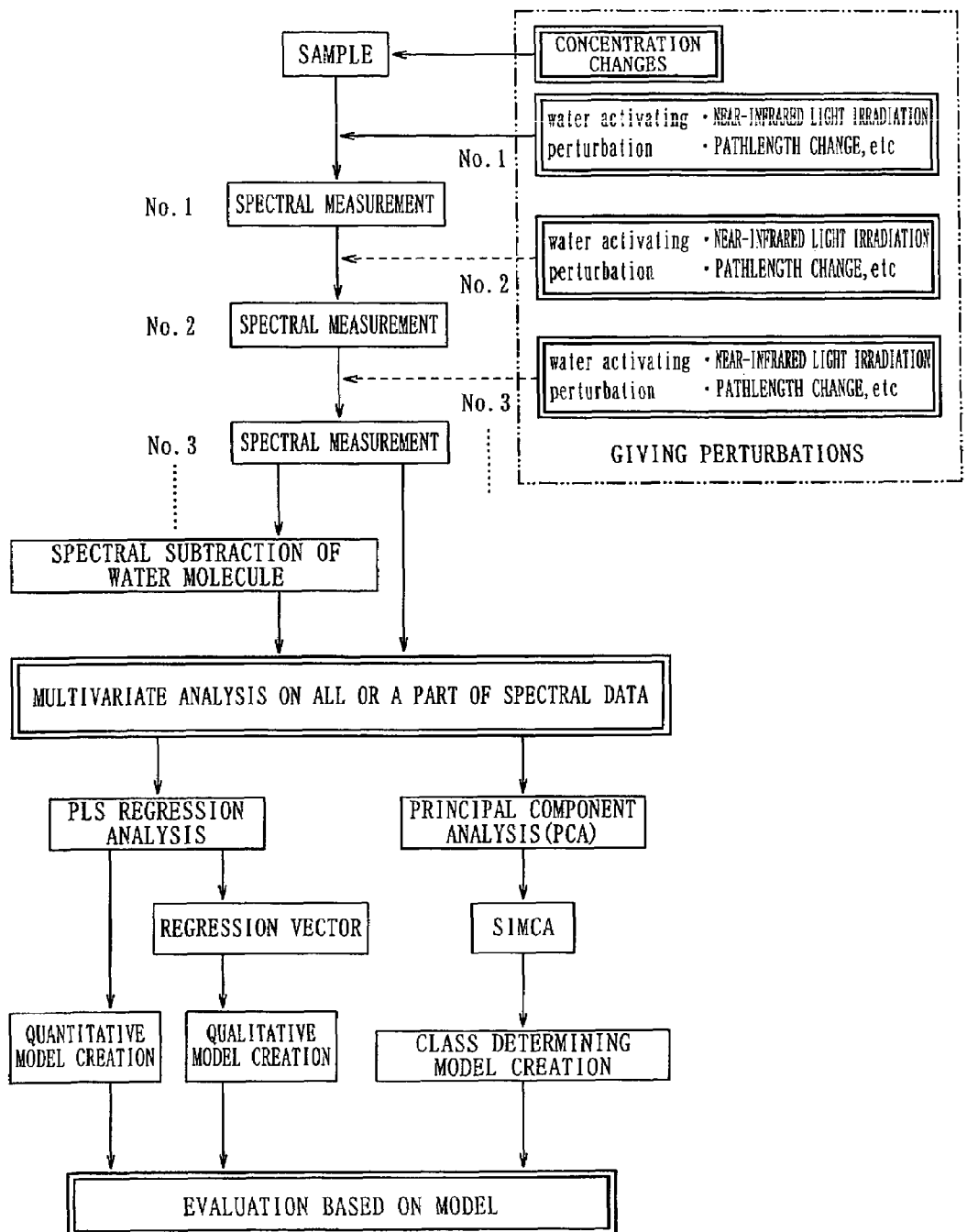
[FIG. 2]
A schematic diagram showing the characteristic portion of the present invention method
Figure 4:
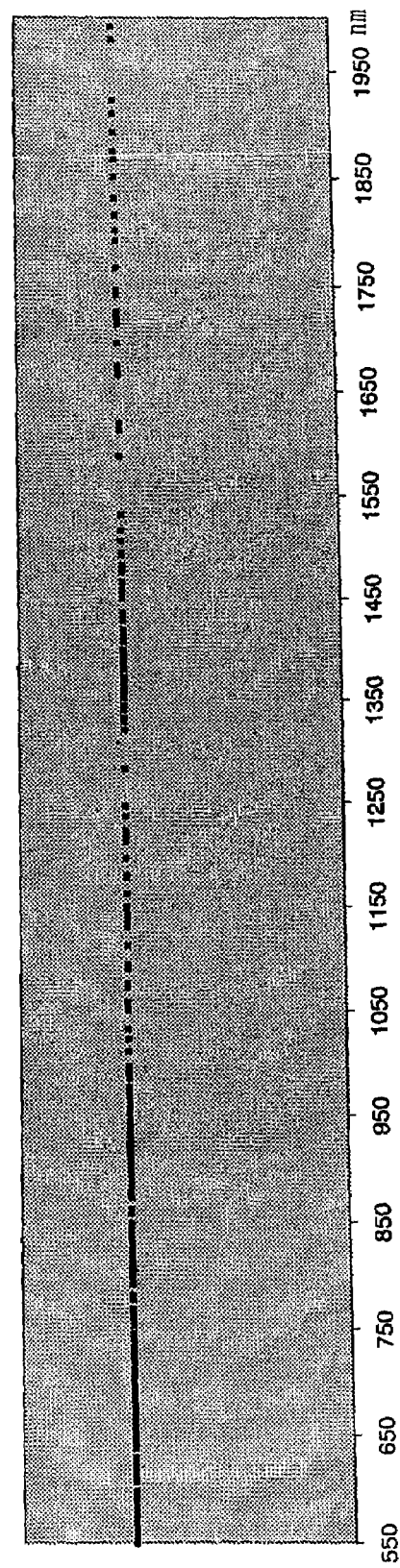
[FIG. 4]
A schematic diagram showing intensity changes of water molecule absorbance band
Figure 5:
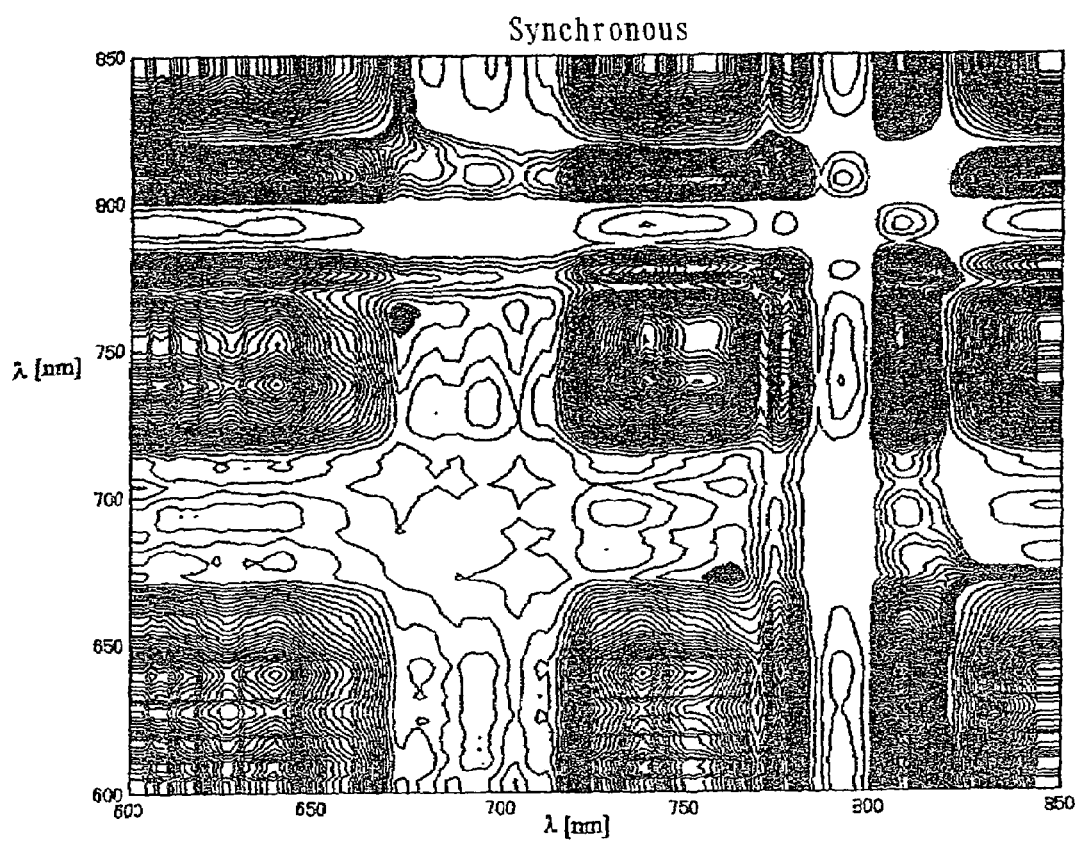
[FIG. 5]
A contour representing intensity changes of water molecule absorbance
Figure 7:
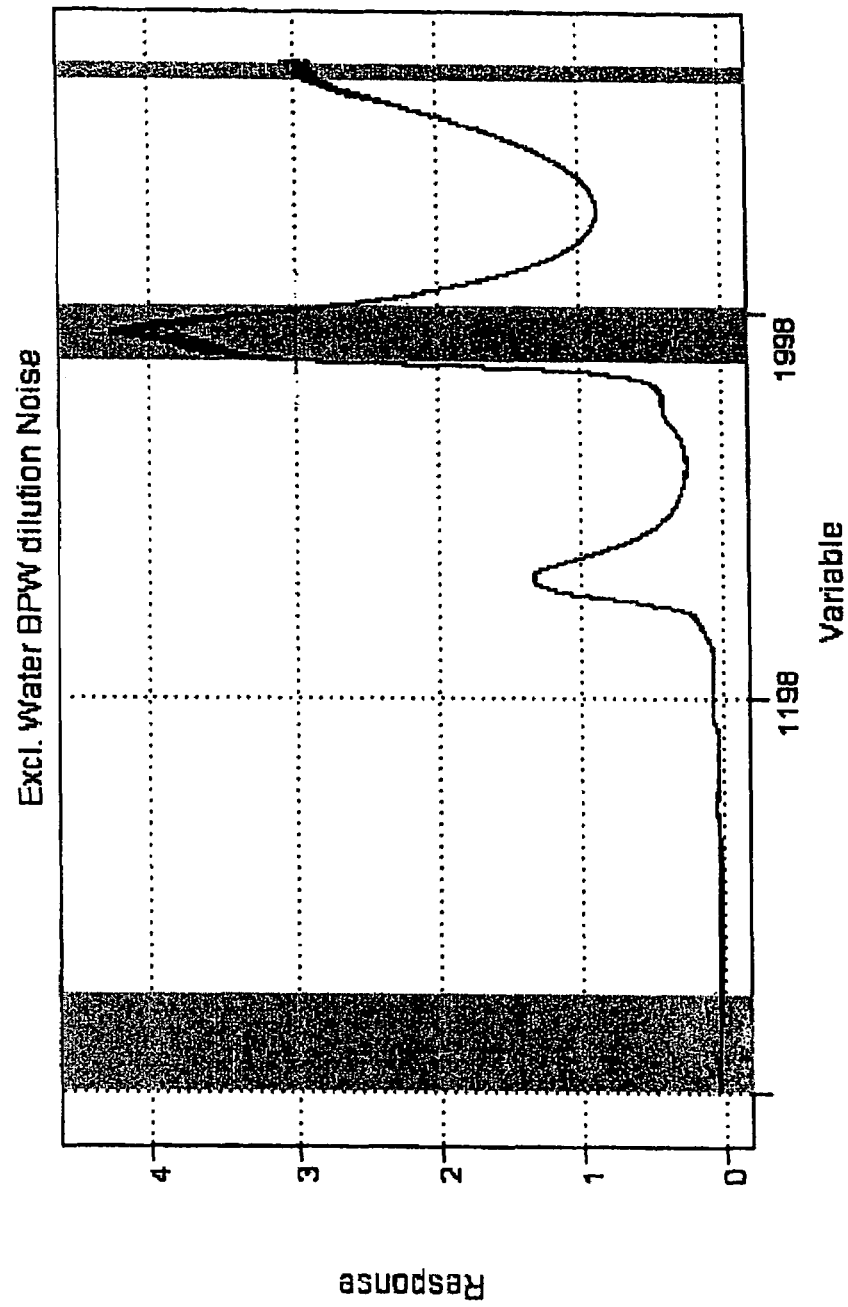
[FIG. 7]
Absorption spectra when bacteria in the sample are measured
Figure 8:
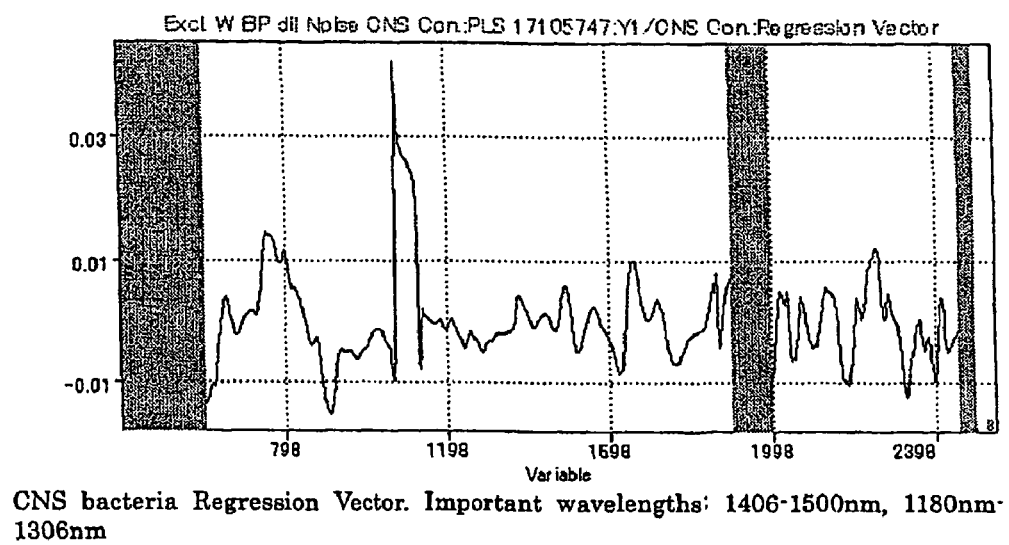
[FIG. 8]
A diagram showing a CNS regression vector
Figure 9:
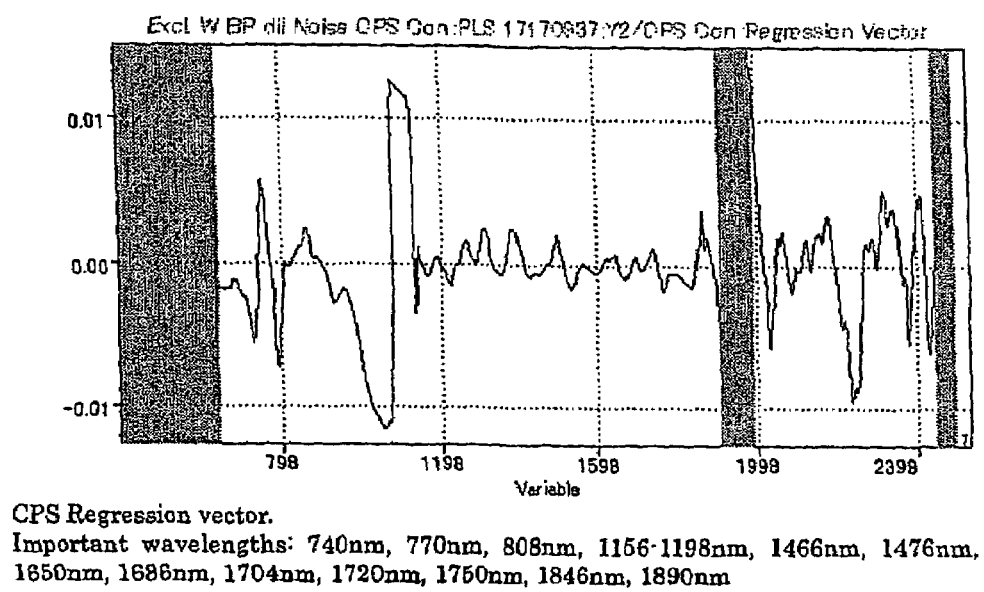
[FIG. 9]
A diagram showing a CPS regression vector
Figure 10:
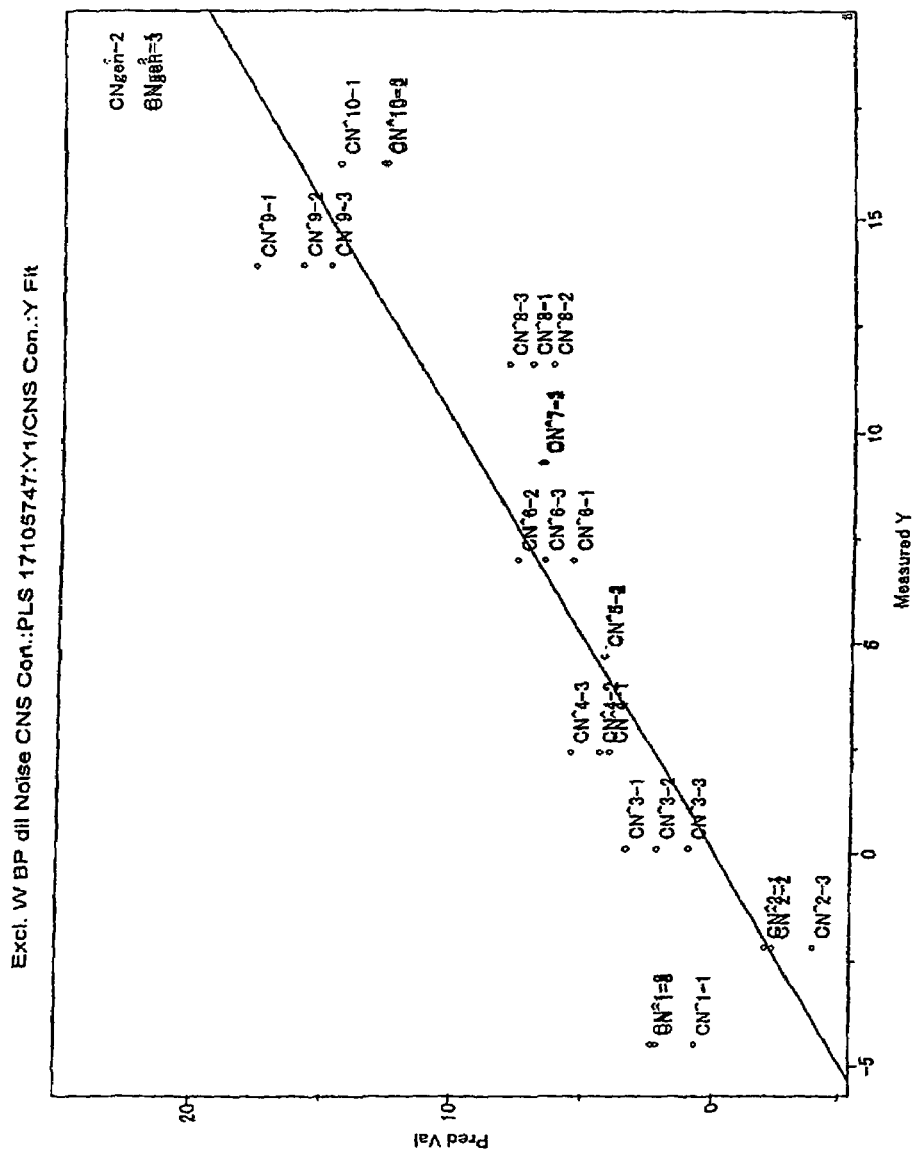
[FIG. 10]
A diagram showing a CNS calibration line
Figure 11:
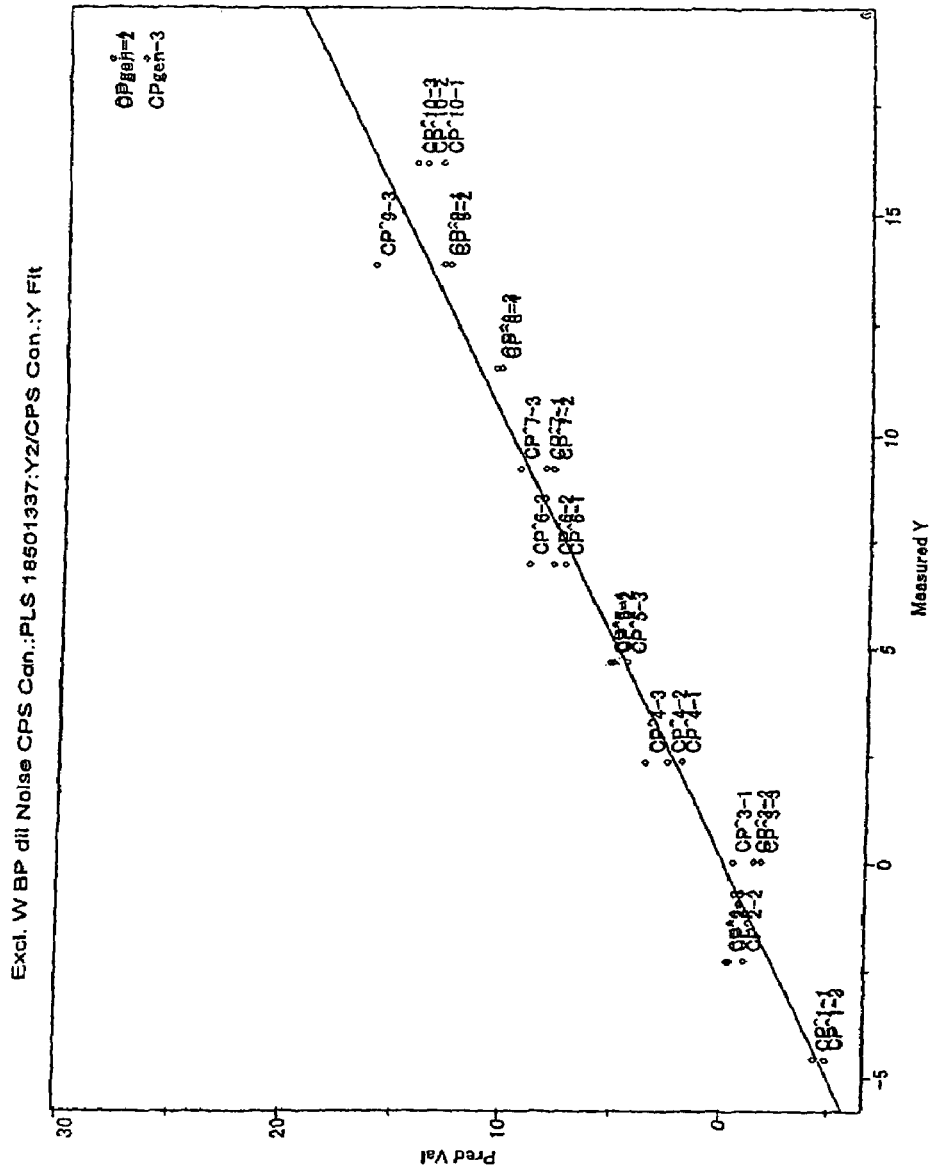
[FIG. 11]
A diagram showing a CPS calibration line
Figure 13:
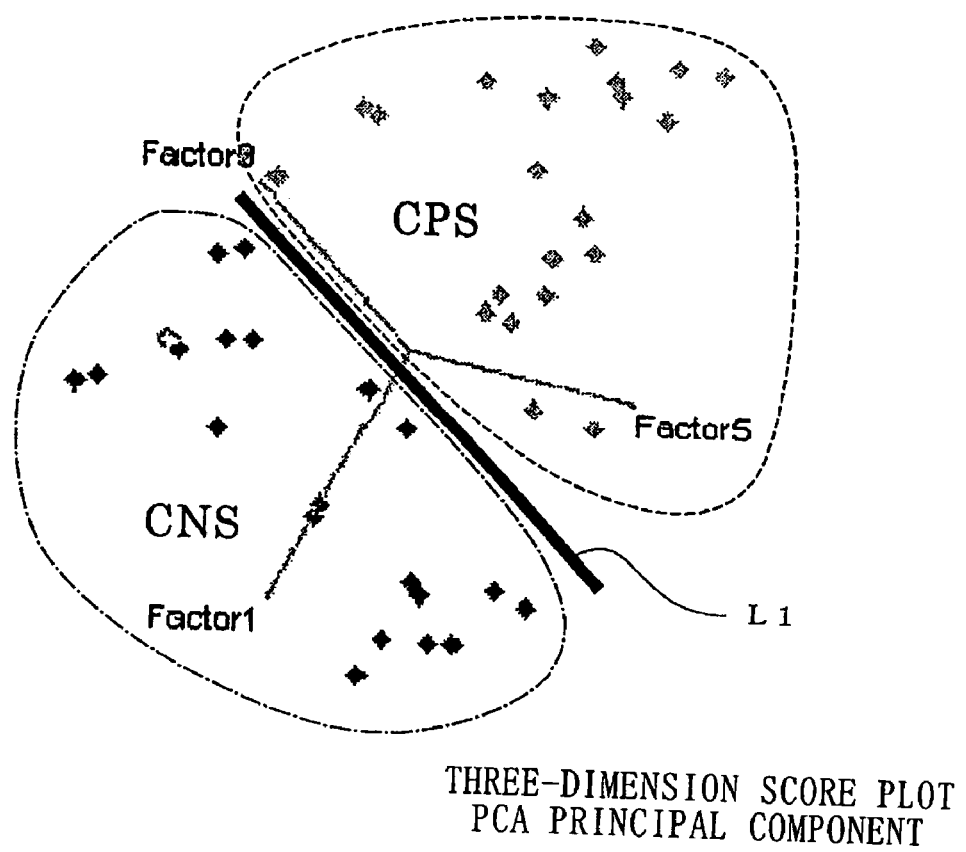
[FIG. 13]
A diagram of three-dimensional plots of CNS and CPS based on a 1st principal component (Factor 1), a 3rd principal component (Factor 3) and a 5th principal component (Factor 5)
Figure 15:
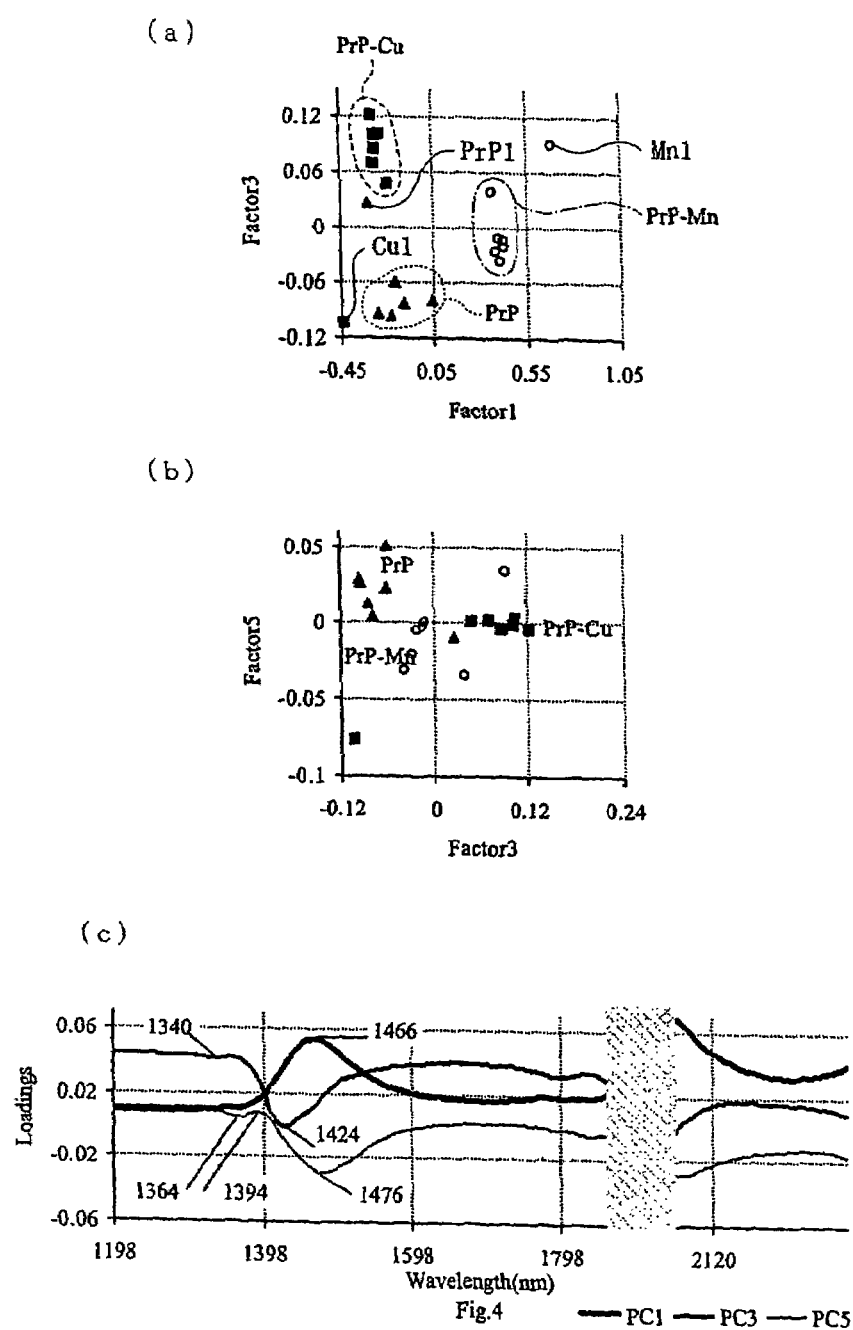
[FIG. 15]
Figure 17:
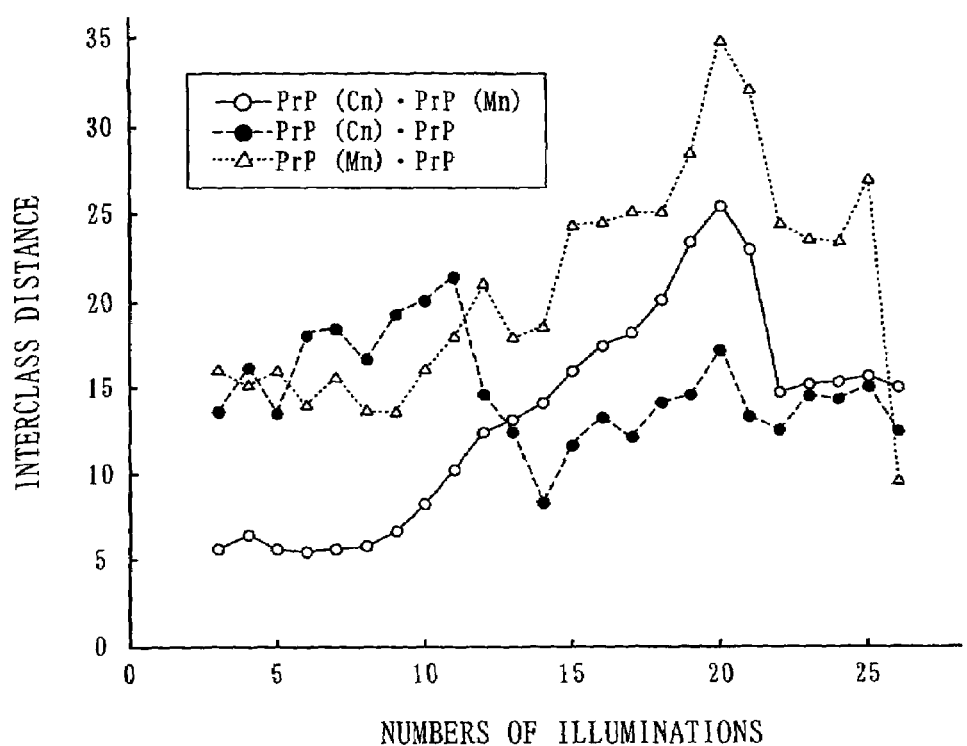

[FIG. 17]
A diagram showing a SIMCA analysis result with repeated illuminations

[FIG. 18]
A diagram showing a result of interclass distance when prion protein concentration is changed

Figure 19:
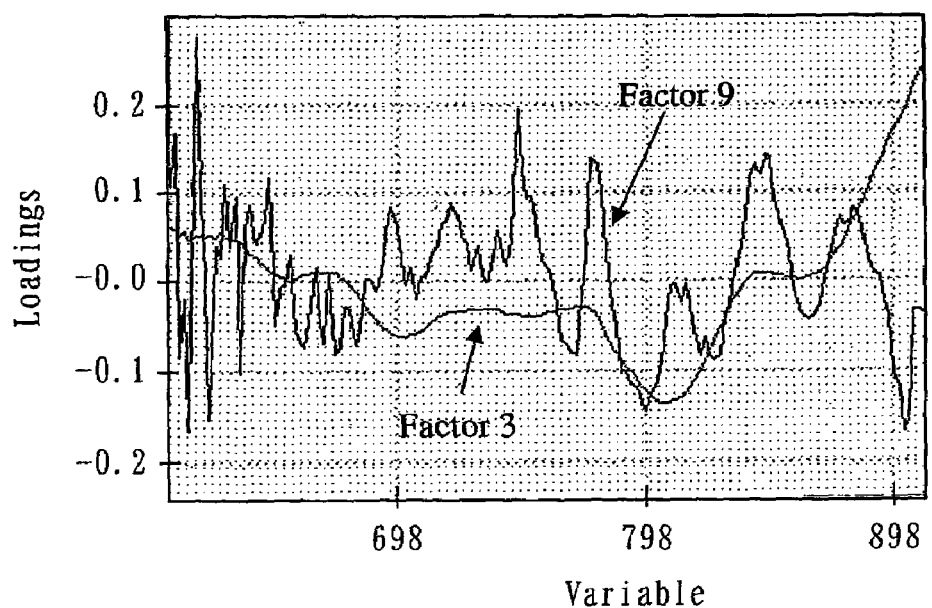

[FIG. 19]
A diagram showing a regression vector when PrP and PrP(Cu) are determined by changing light path-length

Figure 20:
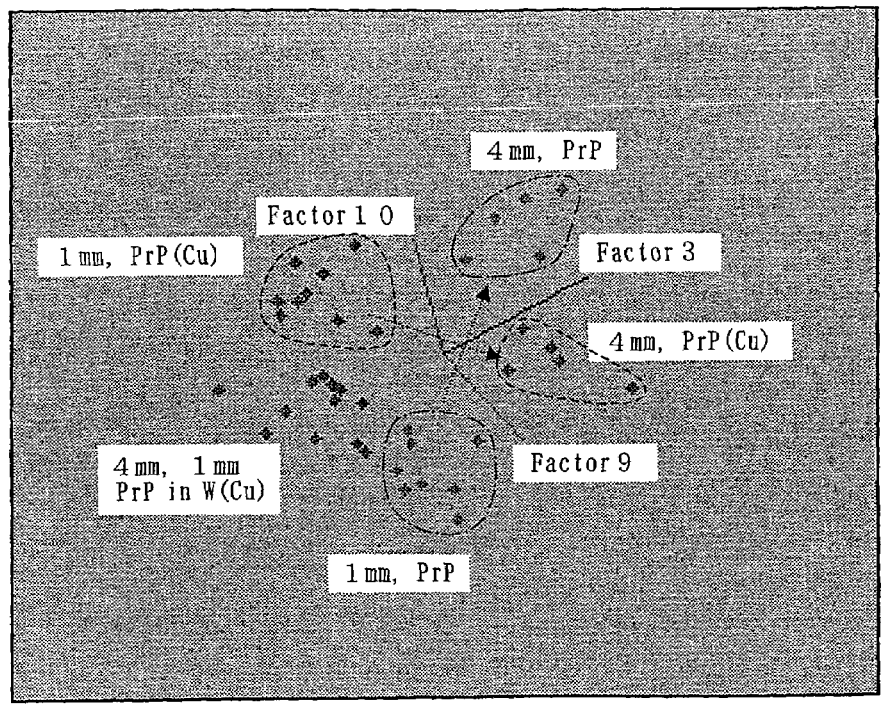

[FIG. 20]
A diagram showing a result of determination of PrP and PrP(Cu) by changing light path-length, (a) A SIMCA analysis result, (b) An interclass distance, and (c) A determination result

[FIG. 21]
A graph showing SIMCA distances when determining prion protein while giving perturbations of different temperature

Figure 22:
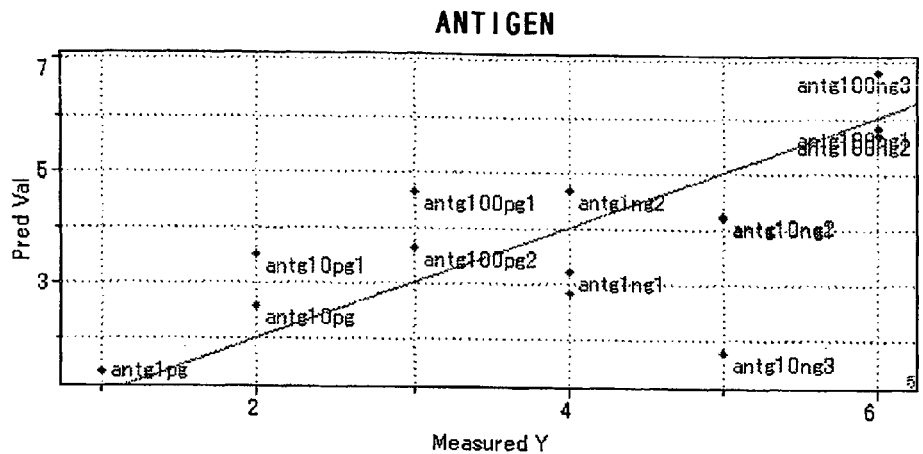

[FIG. 22]
(a) A diagram showing an calibration line when antigen concentration in the sample is measured, (b) A diagram showing a determination result by cross-validation, and (c) A diagram showing interclass distances by the SIMCA analysis

Figure 23:
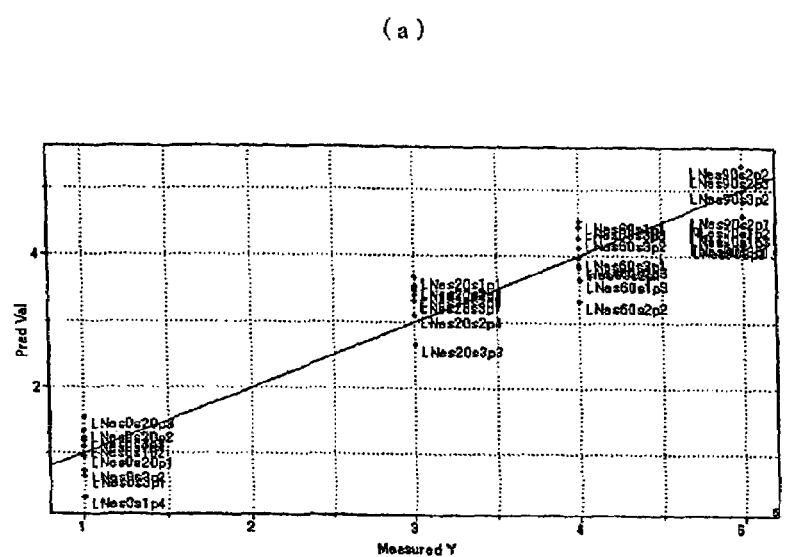

[FIG. 23]
(a) A diagram showing an calibration line when measuring coffee granule diameter before dissolution, (b) A diagram showing an analysis result by cross validation

[FIG. 24]
Diagrams showing examples of determining granule diameter size (a) SIMCA distance when determining coffee granule, (b) SIMCA distance when determining sugar granule, (c) Correlation coefficient and validation difference when measuring sugar granule

Figure 25:
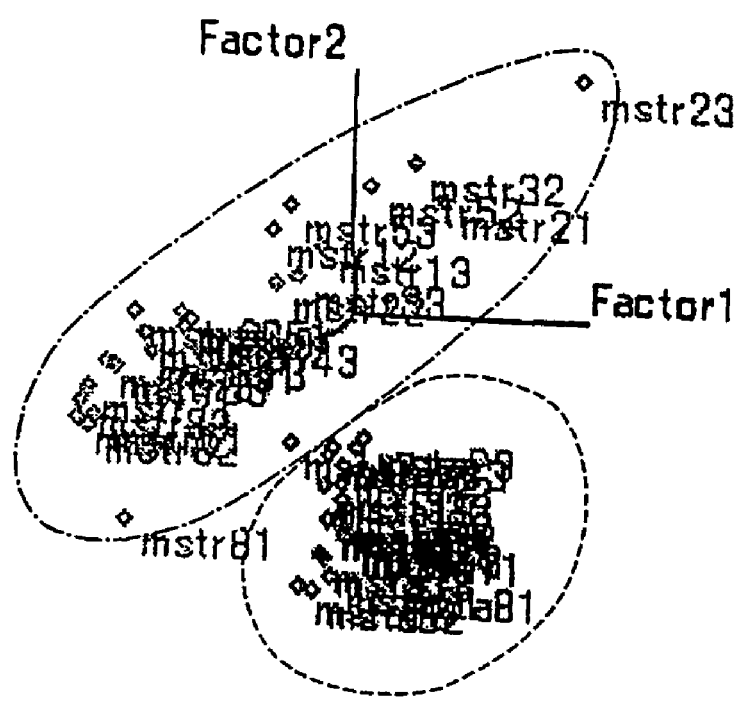

[FIG. 25]
A diagram showing result of determination between msta and mstr with the 1st principal component (Factor 1), the 2nd principal component (Factor 2), and the 3rd principal component (Factor 3) when measuring bacteria in the sample

[FIG. 26]
(a) (b) Diagrams showing results of estimating cow milk component concentration based on blood plasma spectra of the cow, (c) (d) Diagrams showing results of estimating cow blood plasma component concentration based on milk spectra of the cow

[FIG. 27]
(a) (b) Diagrams showing results of estimating cow milk component concentration based on rumen juice spectra of the cow, (c) (d) Diagrams showing results of estimating cow rumen juice component concentration based on milk spectra of the cow

[FIG. 28]
Diagrams showing a silica cell, (a) An overall perspective view (b) A plan view

Figure 29:
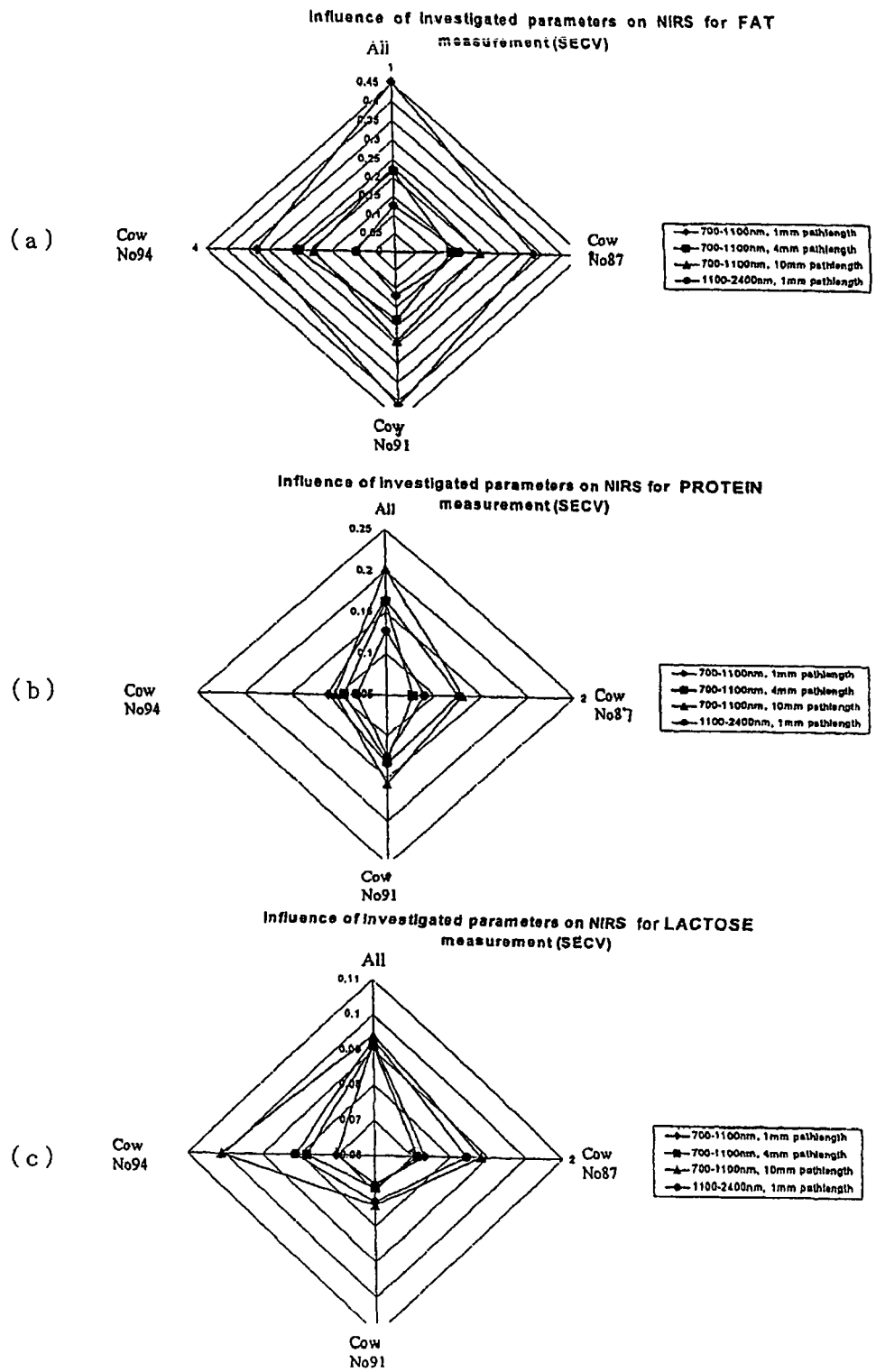

[FIG. 29]
Diagrams showing SECV when measuring a plurality of cow milk component concentrations, (a) SECV pf FAT, (b) SECV of PROTEIN (c) SECV of LACTOSE

Figure 30:
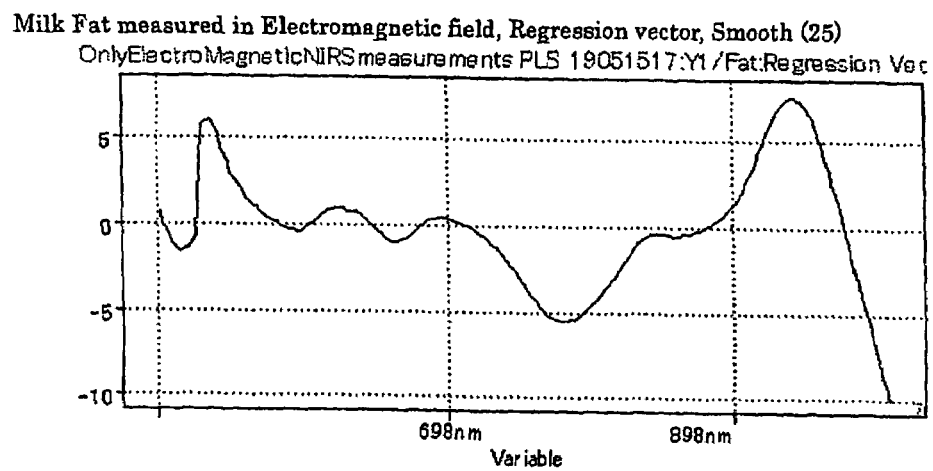

[FIG. 30]
(a) A diagram showing regression vector Y1 when measuring a fat concentration in the cow milk (b) A diagram showing a analysis result by the cross validation

Figure 31:
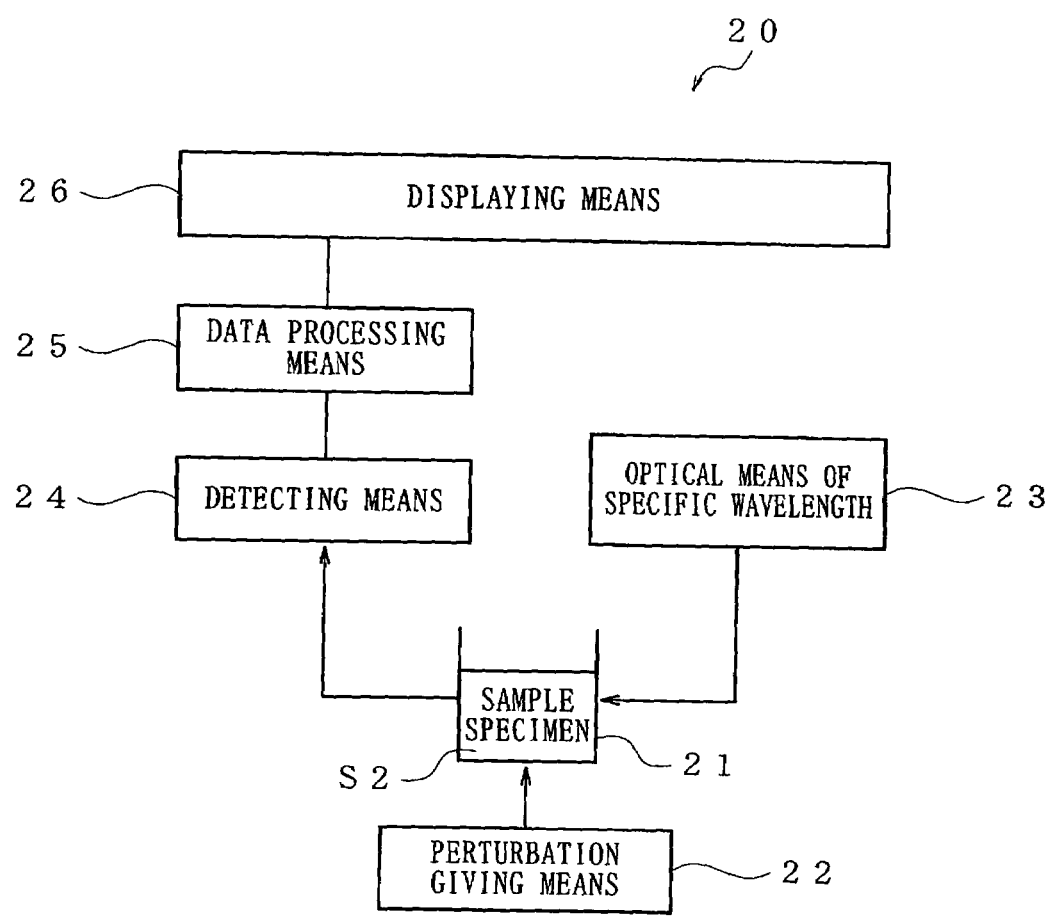

[FIG. 31]
A diagram showing one example of a visible/near-infrared spectrometry device for determining component characteristics

DESCRIPTION OF REFERENCE NUMBER 1 known sample
2 new sample
3 silica cell
3A injection portion of the sample specimen
4 irradiation direction
5 irradiation direction
10 visible/near-infrared spectrometry device
20 visible/near-infrared spectrometry device (for specific components)
L1 boundary
S1 sample specimen
S2 (specific) sample specimen

What is claimed is:

1. A visible/near-infrared spectrometry method comprising steps of:
    irradiating a sample specimen with visible light and/or near-infrared light in the wavelength range 400 nm to 2500 nm or a part of the range;
    analyzing the spectra of transmitted light, reflected light, and/or transmitted/reflected light obtained from said sample specimen;
    determining the presence and/or measuring the characteristics of respective specific components present in said sample specimen,
    wherein said method further comprises steps of:
    measuring spectra while giving predetermined conditions including at least 3 times repeated irradiations as conditions to generate transitional changes of spectral response pattern while activating water existing within and/or around said sample specimen to promote interaction between water molecules and predetermined component included in said sample specimen;
    conducting spectral and/or multivariate analysis to detect transitional changes in spectral response patterns;
    building a model assuming that components of known sample specimen can be determined and/or that characteristics of said components can be measured using the detected transitional changes of the spectral response patterns;
    conducting the same spectral and/or multivariate analysis on unknown (new) sample specimen while giving the same conditions as said predetermined conditions: and,
    comparing with the built models to predict components of unknown sample specimen and/or characteristics of the components.

2. A visible/near-infrared spectrometry method according to claim 1 wherein said predetermined condition changes are perturbations (water activating perturbations: WAP) to induce physical or chemical changes to said sample specimen by activating water existing within and/or around said sample specimen, and the perturbations are any one or a combination of at least 3 times repeated light irradiations, change of sample specimen concentration, extension of irradiation time, electromagnetic force application, light path-length changes, temperature changes, pH changes, and pressure changes.

3. A visible/near-infrared spectrometry method according to claim 2 wherein the perturbations, the concentrations of sample specimen are changed in step value by a factor of 10 (e.g. $10^{-1}$ to $10^{-10}$) to promote interaction between water and predetermined components, and respective concentrations are subjected to at least 3 times repeated irradiations to promote an interaction between water and the predetermined components.

4. A visible/near-infrared spectrometry method according to claim 3 wherein determined are bacteria in said sample specimens and the bacteria are CNS (coagulase-negative *staphylococcus*) and CPS(coagulase-positive *staphylococcus*).

5. A visible/near-infrared spectrometry method according to claim 2, wherein the spectrometry is conducted while giving perturbations in which sample specimen concentrations are changed in step values and respective changed samples are subjected to at least 3 times consecutive repeated irradiations, to detect protein PrP(CU) and/or PrP(Mn) which contain metal component and protein PrP containing no metal component.

6. A visible/near-infrared spectrometry method according to claim 2, wherein the spectrometry is conducted while giving perturbations in which light path-length and/or concentrations are changed and respective changed samples are subjected to at least 3 times consecutive repeated irradiations, to determine protein PrP(metal) containing metal components and protein PrP containing no metal components.

7. A visible/near-infrared spectrometry method according to claim 2, wherein the spectrometry is conducted while giving perturbations in which sample specimen concentrations are changed in step values by a factor of 10 and respective changed samples are subjected to repeated irradiations, to measure antigen concentrations in the sample specimen.

8. A visible/near-infrared spectrometry method according to claim 2, wherein the spectrometry is conducted while giving perturbations in which sample specimen concentrations are changed in step values and respective changed samples are subjected to at least 3 times consecutive repeated irradiations, to measure a diameter of granule in pre-dissolved state of the granule dissolved in the sample.

9. A visible/near-infrared spectrometry method according to claim 2, wherein the spectrometry is conducted while giving perturbations in which sample specimen concentrations are changed in step values by a factor of 10 and respective changed samples are subjected to at least 3 times consecutive repeated irradiations, to determine different types of bacteria in the sample specimen.

10. A visible/near-infrared spectrometry method according to claim 2, wherein the spectrometry is conducted while giving perturbations in which the spectrometry is conducted at least one time each in the morning and in the evening per day for a plurality of consecutive days, and the spectrometry is again conducted at least one time each in the morning and in the evening per day for a plurality of consecutive days after feeds are changed, to estimate component concentrations of biological fluids including blood plasma and rumen juice of mammals such as cows based on raw milk spectra of the mammals.

11. A visible/near-infrared spectrometry method according to claim 2, wherein the spectrometry is conducted while giving perturbations in which the spectrometry is conducted at least one time each in the morning and in the evening per day for a plurality of consecutive days, and the spectrometry is again conducted at least one time each in the morning and in the evening per day for a plurality of consecutive days after feeds are changed, to estimate component concentrations of raw milk of the mammals such as cows based on the spectra of biological fluids including blood plasma and rumen juice of the mammals.

12. A visible/near-infrared spectrometry method according to claim 2, wherein the spectrometry is conducted while giving perturbations in which light path-length are changed and respective changed samples are subjected to at least 3 times consecutive repeated irradiations and the spectrometry is conducted only in first wavelength range, or conducted in the first and second wavelength range, said first wavelength being in range from 700 nm to 1100 nm and said second wavelength being in range from 1100 nm to 2400 nm, to measure concentrations of plural components of raw milk.

13. A visible/near-infrared spectrometry method according to claim 2, wherein the spectrometry is conducted while giving perturbations in which 10 V. voltage is applied and light in the wavelength range from 500 to 1000 nm is consecutively irradiated at least 3 times, to measure fat concentrations of raw milk.

14. A visible/near-infrared spectrometry device comprising:
a near-infrared light generating means capable of irradiating a sample specimen with near-infrared light or visible and/or near-infrared light in the wavelength range from 400 nm to 2500 nm or part of that range;
an optical means for irradiating said visible light and/or near-infrared light to the sample specimen;
a detecting means for obtaining spectra of transmitted light, reflected light, or transmitted/reflected light from said sample specimen; and
a data processing means for conducting a predetermined multivariate analysis on obtained spectra,
wherein the visible/near-infrared spectrometry device further comprises: a perturbation giving means for giving perturbations by adding predetermined condition changes to the sample to generate transitional changes in spectral response to activate water existing within and/or around said sample specimen to promote interaction between water molecules and specific component included in said sample specimen; and
said data processing means conducting a spectral analysis on all or a part of the wavelength range of spectral responses obtained by giving perturbations.

15. A visible/near-infrared spectrometry device according to claim 14, wherein said perturbation giving means expose the sample specimen to water activating perturbations (WAP) to induce physical or chemical changes to said sample specimen by activating water existing within and/or around said sample specimen, and comprises an irradiation controlling unit for controlling irradiation time and number of irradiations are provided.

16. A visible/near-infrared spectrometry device according to claim 15, wherein said perturbation giving means comprises at least one of means capable of adjusting electromagnetic power, changing light path-length, and changing temperature; and a controlling means for controlling perturbations given by said perturbation giving means and operation timing between irradiating light and receiving light so as to irradiate light and receive light from probes which comprises said optical means and said detecting means together or separately and perform data processing.

17. A visible/near-infrared spectrometry device according to claim 16, wherein said data processing means execute the spectral analysis of the responses to specific perturbations followed by data analysis for all or part of several distinct wavelengths ranges will allow the detection of bio-macromolecular structures and functions and these changes.

18. A visible/near-infrared spectrometry device comprising:

a sample specimen containing unit;

a perturbation giving means for giving perturbations by adding predetermined changes to the sample specimen to generate transitional changes in spectral response to activate water existing within and/or around said sample specimen to promote interaction between water molecules and specific component included in said specimen;

an optical means for irradiating visible light and/or near-infrared light in the wavelength range 400 nm to 2500 nm or a part of the range to the sample specimen, said lights being in a predetermined specific wavelength range corresponding to the sample specimen;

a detecting means for obtaining spectra of transmitted light, reflected light, or transmitted/reflected light from the sample specimen;

a data processing means for conducting a predetermined multivariate analysis on obtained spectra; and a displaying means for display a measurement result.

19. A visible/near-infrared spectrometry device according to claim 18, wherein important wavelengths ranges which are optimal for measuring respective sample specimens are predetermined.

* * * * *